US008142805B1

(12) United States Patent
Vyavahare et al.

(10) Patent No.: US 8,142,805 B1
(45) Date of Patent: Mar. 27, 2012

(54) IMPLANTABLE DEVICES INCLUDING FIXED TISSUES

(75) Inventors: Narendra R. Vyavahare, Easley, SC (US); Devanathan Raghavan, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 1077 days.

(21) Appl. No.: 11/934,844

(22) Filed: Nov. 5, 2007

Related U.S. Application Data

(60) Provisional application No. 60/857,062, filed on Nov. 6, 2006, provisional application No. 60/858,011, filed on Nov. 9, 2006.

(51) Int. Cl.
*A61K 38/54* (2006.01)
*C12N 5/02* (2006.01)

(52) U.S. Cl. ....... 424/422; 424/400; 424/94.1; 435/325; 435/183

(58) Field of Classification Search .................. 435/325, 435/183; 424/400, 422, 94.1
See application file for complete search history.

(56) References Cited

U.S. PATENT DOCUMENTS

| | | | |
|---|---|---|---|
| 4,378,224 A | 3/1983 | Nimni et al. | |
| 4,655,773 A | 4/1987 | Grassi | |
| 4,801,299 A | 1/1989 | Brendel et al. | |
| 5,081,157 A | 1/1992 | Pomerantz | |
| 5,397,353 A | 3/1995 | Oliver et al. | |
| 5,512,291 A | 4/1996 | Li | |
| 5,716,370 A | 2/1998 | Williamson, IV et al. | |
| 5,990,379 A | 11/1999 | Gregory | |
| 6,001,126 A | 12/1999 | Nguyen-Thien-Nhon | |
| 6,102,944 A | 8/2000 | Huynh et al. | |
| 6,110,206 A | 8/2000 | Stone | |
| 6,210,957 B1 | 4/2001 | Carpentier et al. | |
| 6,214,054 B1 | 4/2001 | Cunanan et al. | |
| 6,245,105 B1 | 6/2001 | Nguyne et al. | |
| 6,267,834 B1 | 7/2001 | Shannon et al. | |
| 6,331,319 B1 | 12/2001 | Badylak et al. | |
| 6,338,740 B1 | 1/2002 | Carpentier | |
| 6,342,070 B1 | 1/2002 | Nguyen-Thien-Nhon | |
| 6,391,538 B1 | 5/2002 | Vyavahare et al. | |
| 6,402,780 B2 | 6/2002 | Williamson, IV et al. | |
| 6,454,799 B1 | 9/2002 | Schreck | |
| 6,461,382 B1 | 10/2002 | Cao | |
| 6,479,079 B1 | 11/2002 | Pathak et al. | |
| 6,506,197 B1 | 1/2003 | Rollero et al. | |
| 6,517,824 B1 | 2/2003 | Kohn et al. | |
| 6,532,388 B1 | 3/2003 | Hill et al. | |
| 6,547,827 B2 | 4/2003 | Carpentier et al. | |
| 6,558,418 B2 | 5/2003 | Carpentier et al. | |
| 6,561,970 B1 | 5/2003 | Carpentier et al. | |
| 6,645,764 B1 | 11/2003 | Adkisson | |
| 6,824,970 B2 | 11/2004 | Vyavahare et al. | |
| 6,861,211 B2 | 3/2005 | Levy et al. | |
| 2003/0078659 A1 | 4/2003 | Yang | |
| 2003/0138950 A1 | 7/2003 | McAllister et al. | |
| 2004/0153145 A1 | 8/2004 | Simionescu et al. | |
| 2005/0142163 A1* | 6/2005 | Hunter et al. | .................. 424/423 |
| 2005/0187639 A1* | 8/2005 | Hunter et al. | ............... 623/23.72 |

OTHER PUBLICATIONS

Narendra Vyavahare, et al.; Mechanisms of bioprosthetic heart valve failure: Fatigue causes collagen denaturation and glycosaminoglycan loss; pp. 44-50; Jul. 1999 Biomed Mat. Res.
Joshua J. Lovekamp, et al.; Stability and function of glycosaminoglycans in porcine bioprosthetic heart valves; pp. 1507-1518, Mar. 27(8) 2006 Biomaterials.
Dant T. Simionescu et al.; Glycosaminoglycan-degrading enzymes in porcine aortic heart vales: Implications for bioprosthetic heart valve degeneration; pp. 217-225; Mar. 12, 2003 J Heart Valve Dis, vol. 12 No. 2.
Am J. Cardiol. Mar. 15, 1984 53(7) 941-4.
Isenburg et al., "Tannic acid treatment enhances biostability and reduces calcification of glutaraldehyde fixed aortic wall." *Biomaterials*, 26 (2005): 1237-1245.
Isenburg et al., "Elastin stabilization in cardiovascular implants: improved resistance to enzymatic degradation by treatment with tannic acid." *Biomaterials*, 25 (2004): 3293-3302.
Isenburg, et al., "Structural requirements for stabilization of vascular elastin by polyphenolic tannins." *Biomaterials*, 27 (2007): 3645-3651.
Kasyanov et al., "Tannic acid mimicking dendrimers as small intestine submucosa stabilizing nanomordants." *Biomaterials*, 27 (2006): 745-751.
Lis, et al., "Biochemical characterization of individual normal, floppy and rheumatic human mitral valves." *Biochemical Journal*, 244 (1987): 597-603.
Schoen et al., "Calcification of Bovine Pericardium Used in Cardiac Valve Bioprostheses." *American Journal of Pathology*, 123 (1986):134-145.
Wei, et al., "Construction of varying porous structures in acellular bovine pericardia as a tissue-engineering extracellular matrix." *Biomaterials*, 26 (2005): 1905-1913.

* cited by examiner

*Primary Examiner* — Ruth Davis
(74) *Attorney, Agent, or Firm* — Dority & Manning, P.A.

(57) ABSTRACT

Disclosed are implantable tissues including one or more enzyme inhibitors bound in the tissues, bioprostheses including the tissue, and methods for incorporating enzyme inhibitors in implantable tissues. Disclosed tissue can exhibit increased resistance to degradation, and specifically, degradation due to enzyme activity following implantation. Moreover, the disclosed methods can lead to increased levels of beneficial components bound in implantable tissues following a fixation/stabilization protocol. Increased levels of beneficial agents in an implantable tissue can further improve the implantable tissues and bioprostheses incorporating the tissues through improved mechanical characteristics and longer lifespan.

16 Claims, 20 Drawing Sheets

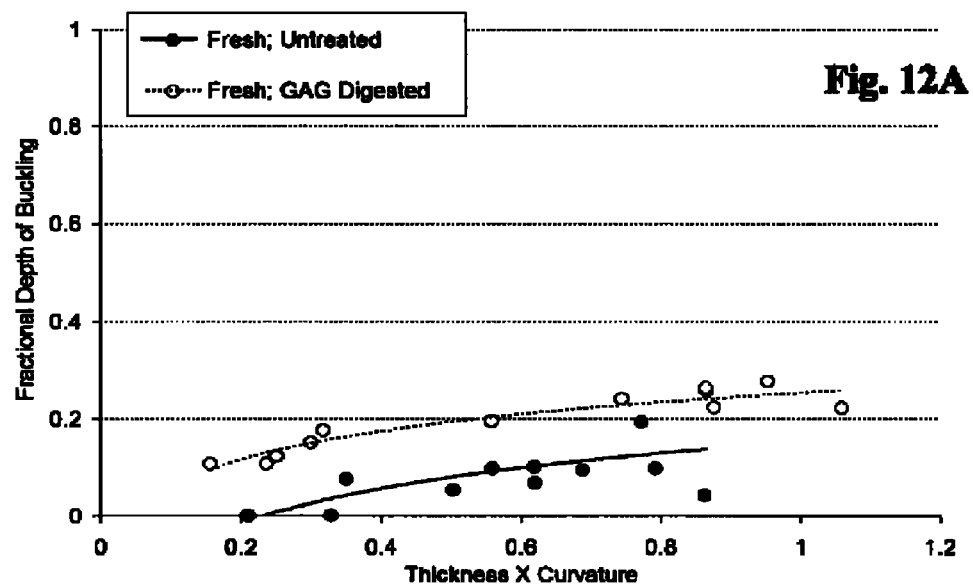
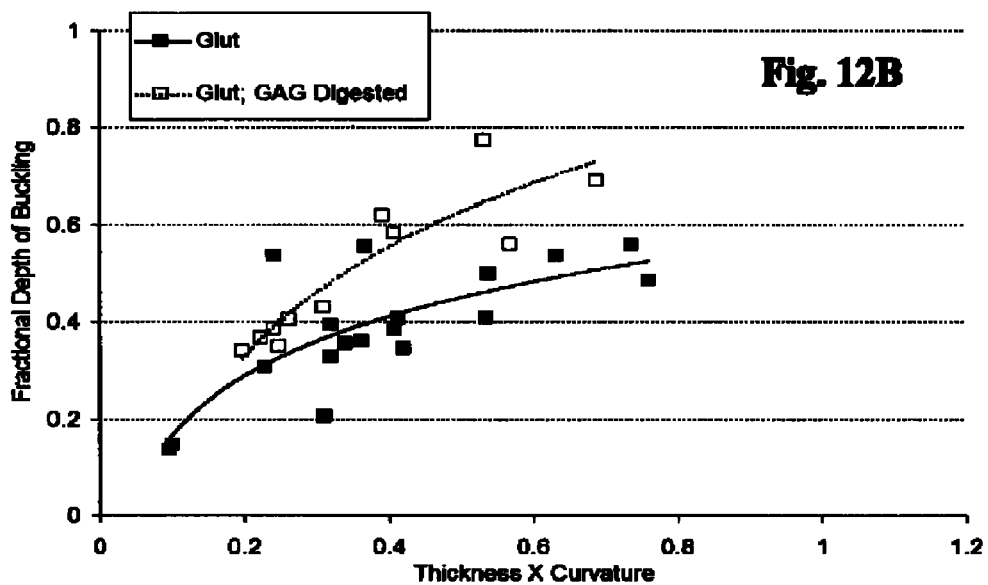

IMPLANTABLE DEVICES INCLUDING FIXED TISSUES

CROSS REFERENCE TO RELATED APPLICATIONS

This application claims filing benefit of U.S. Provisional Patent Application having Ser. No. 60/857,062 having a filing date of Nov. 6, 2006 and U.S. Provisional Patent Application having Ser. No. 60/858,011 having a filing date of Nov. 9, 2006, both of which are incorporated herein by reference in their entirety.

FEDERALLY SPONSORED RESEARCH AND DEVELOPMENT

The United States Government may have rights in this invention pursuant to Contract No. HL 070969 between Clemson University and the National Institutes of Health.

BACKGROUND

Implantable prosthetics such as prosthetic heart valves can be used to replace damaged or diseased tissues. For instance, prosthetic heart valves may be used to replace natural valves including aortic, mitral, and pulmonary valves. The predominant types of prosthetic heart valves are either mechanical valves or bioprosthetic valves. Bioprosthetic valves include allograft valves, which include biomaterial supplied from human cadavers; autologous valves, which include biomaterial supplied from the individual receiving the valve; and xenograft valves, which include biomaterial obtained from non-human biological sources including pigs, cows or other animals.

Presently, mechanical valves have the longest durability of available replacement heart valves. However, implantation of a mechanical valve requires a recipient to be prescribed anticoagulants to prevent formation of blood clots. Unfortunately, continuous use of anticoagulants can be dangerous, as it greatly increases the user's risk of serious hemorrhage. In addition, a mechanical valve can often be audible to the recipient and may fail without warning, which can result in serious consequences, even death.

The use of bioprosthetic heart valves (BPHVs) in valve replacement procedures is often preferred as BPHVs do not require ongoing patient treatment with anticoagulants. Allograft transplants have been quite effective, with good compatibility and blood flow characteristics in the recipients. However, the availability of human valves for transplantation continues to decline as a percentage of cardiac surgeries performed each year. As such, the choice of xenograft materials for use in replacement BPHVs is becoming more common.

Both xenografts and allografts require that the graft biomaterial be chemically fixed prior to use in order to render the biomaterial more non-antigenic as well as to improve resistance of the biomaterial to degradation. Currently, glutaraldehyde fixation of xenograft and allograft biomaterial is used. Glutaraldehyde fixation forms covalent cross-links between free amines in the tissue proteins. Glutaraldehyde is commonly used alone as well as in combination with a variety of other compounds in stabilizing tissues for implant. For instance, traditional glutaraldehyde fixation methods are adequate for fixing certain tissue proteins, and in particular, collagen, but this method is not adequate for fixing other extra cellular matrix components of a tissue. For example, glycosaminoglycans (GAGs) are not fixed via glutaraldehyde crosslinking regimes. As GAGs of the spongiosa layer can act as a cushion between the outer fibrosa and ventricularis layers during function, the leaching of GAGs from implantable materials can lead to reduced bending stiffness and ultimately to degenerative failure of the implant. Attempts have been made to stabilize GAGs in implantable tissues. While these methods have shown some success in preventing degradation of implant materials, room for improvement exists.

Stabilization regimes used alone or in conjunction with glutaraldehyde fixation protocols include use of polyepoxy amines for crosslinking a variety of amino acid residues found in tissue proteins (see, e.g., U.S. Pat. No. 6,391,538 to Vyavahare, et al., which is incorporated herein by reference), use of phenolic tannins for elastin fixation (see, e.g., U.S. Patent Application Publications 2004/0153145 to Simionescu, et al., which is incorporated herein by reference), and use of various chemistries including carbodiimide chemistry for stabilization of glycosaminoglycans in biological tissues (see, e.g., U.S. Pat. No. 6,861,211 to Levy, et al., which is incorporated herein by reference).

Despite advances in addressing the needs for longer lasting and better performing implantable bioprosthetics, there remains room for variation and improvement within the art.

SUMMARY

Disclosed in one embodiment is an implantable tissue that includes an enzyme inhibitor bound to the tissue. More specifically, a non-endogenous enzyme inhibitor can be bound in or on the tissue that can prevent an enzyme from degrading some component of the tissue. For example, the enzyme inhibitor can prevent an enzyme from degrading an extra cellular matrix component of the tissue. In one preferred embodiment, the enzyme inhibitor can prevent an enzyme from degrading one or more glycosaminoglycans of the tissue.

The enzyme inhibitor can be, for example, a sulfated oligosaccharide. In one embodiment, the enzyme inhibitor can be neomycin or a salt thereof (e.g., the sulfate salt of neomycin).

An implantable tissue as disclosed herein can also be stabilized according to other methods, in addition to the binding of an enzyme inhibitor. For example, a tissue can include covalently bound glycosaminoglycans, crosslinked proteins (e.g., collagen and/or elastin), and the like.

In one embodiment, an implantable tissue as disclosed herein can be a component of an implantable bioprosthetic such as a bioprosthetic heart valve. For instance, an implantable tissue including an enzyme inhibitor can be directly or indirectly attached to a support material, e.g., a stent, a suture ring, or the like.

Methods for forming implantable tissues including enzyme inhibitors are also disclosed. For instance, an enzyme inhibitor can be either directly or indirectly bound (e.g., via a heterobifunctional reagent) to a component of the tissue. In one embodiment, an enzyme inhibitor can be bound to the component that is protected by the enzyme inhibitor, i.e., a component that the inhibited enzyme could degrade, but for the presence of the inhibitor in the tissue. Disclosed methods can also incorporate other tissue stabilization protocols including one or more of glycosaminoglycan stabilization protocols, collagen crosslinking protocols, elastin crosslinking protocols, and the like.

BRIEF DESCRIPTION OF THE FIGURES

A full and enabling description of the disclosed subject matter, including the best mode thereof, to one of ordinary skill in the art, is set forth more particularly in the remainder of the specification, including reference to the accompanying figures in which.

DETAILED DESCRIPTION

Figure 1A:
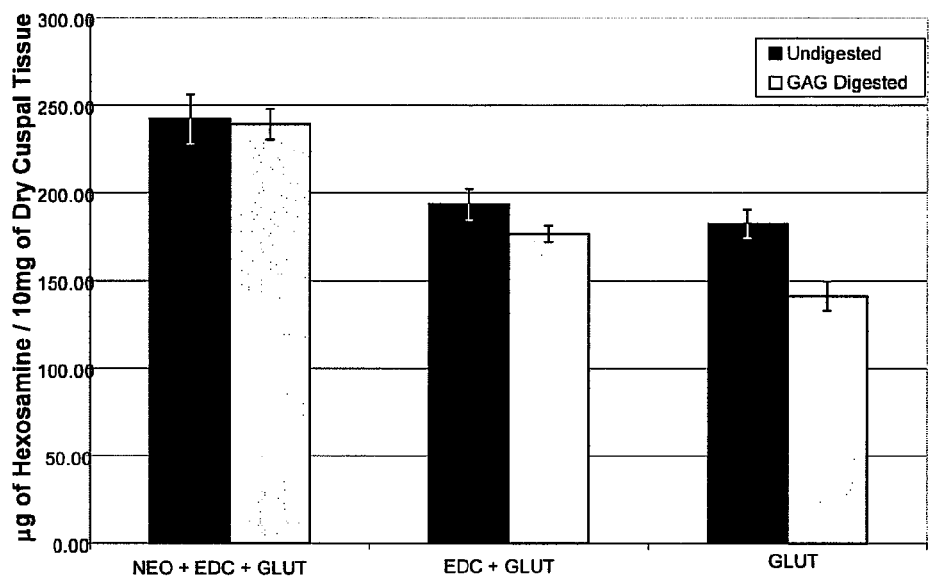
FIG. 1 is a graph setting forth the results of hexosamine assay on cuspal tissues after fixation according to one of three different fixation regimes, GAG digestion, and storage for 1 month (FIG. 1A), four months (FIG. 1B), six months (FIG. 1C), and twelve months (FIG. 1D) in a 0.2% glutaraldehyde solution.
Figure 1B:
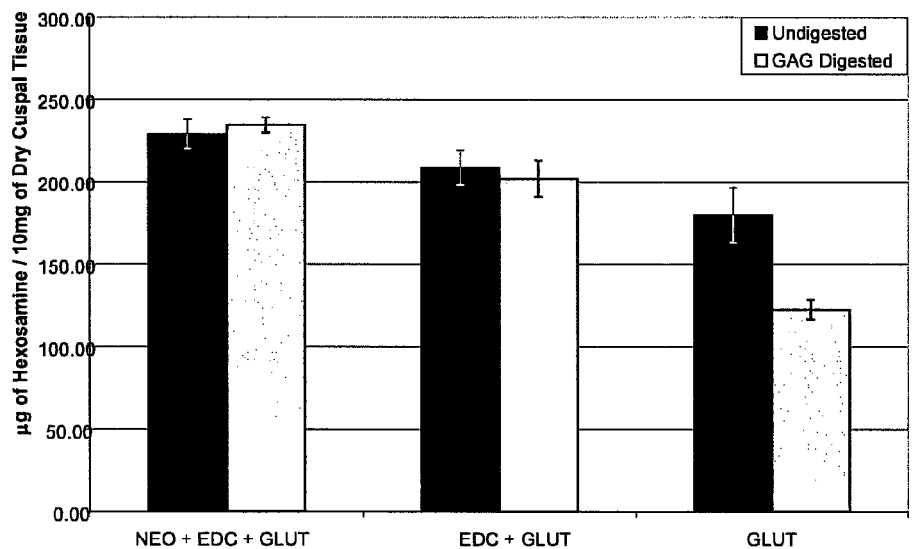
Figure 1C:
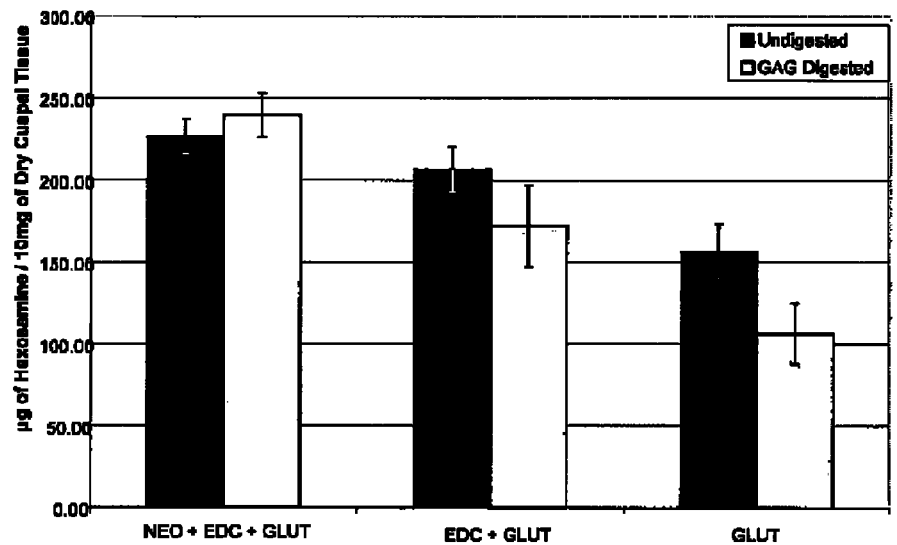
Figure 1D:
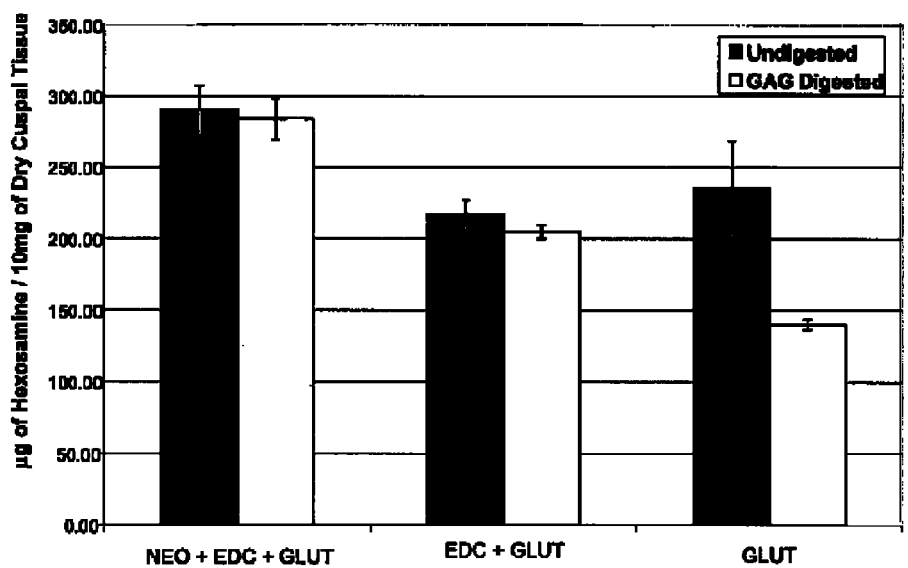

Reference now will be made in detail to embodiments of the disclosed subject matter, one or more examples of which are set forth below. Each example is provided by way of explanation, not limitation of the subject matter. In fact, it will be apparent to those skilled in the art that various modifications and variations can be made without departing from the scope or spirit of the disclosure. For instance, features illustrated or described as part of one embodiment can be used on another embodiment to yield a still further embodiment. Thus, it is intended that the present disclosure cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects, which broader aspects are embodied in the exemplary constructions.

DEFINITIONS

As used herein the term "bioprosthesis" includes any prosthesis which is derived in whole or in part from human, animal, or other organic tissue and which can be implanted into a human or an animal. For example, the term "bioprosthesis" can include, without limitation, an artificial heart, a heart valve prosthesis, an annuloplasty ring, a dermal graft, a vascular graft, a vascular, cardiovascular, or structural stent, a vascular or cardiovascular shunt, a dura mater graft, a cartilage graft, a cartilage implant, a pericardium graft, a ligament prosthesis, a tendon prosthesis, a urinary bladder prosthesis, a pledget, a suture, a permanently or temporary in-dwelling percutaneous device, an artificial joint, an artificial limb, a bionic construct (i.e. a bioprosthesis comprising a microprocessor or other electronic component), and a surgical patch.

As used herein, the term "tissue" is intended to include any natural or synthetic material derived from an organic source and which may be implanted in a mammal. For instance, in addition to natural tissues, the term can include synthetic analogs of natural tissues such as tissue engineered constructs that can include natural biological components, synthetic components, or combinations of such. While exemplary forms of a tissue are described herein, the term "tissue" is not limited to the exemplary embodiments but may include other types of tissues having properties similar to the exemplary tissue.

As used herein, the term "crosslink" refers generally to the process of forming bonds, e.g., covalent bonds, between free, active moieties on or within tissue or between a crosslinking agent or other compound which reacts with a reactive moiety of a tissue. The resulting crosslinked tissue can be considered fixed.

As used herein, the term "fixed," and "stabilized," and grammatical forms thereof are used interchangeably and refer to tissue that has been treated so as to be less antigenic and less susceptible to physical and/or biological degradation. The terms can refer to methods for increasing the mechanical strength of a tissue or a bioprosthesis incorporating a tissue, decreasing the rate or incidence of degradation of a tissue or a bioprosthesis incorporating a tissue following its in vivo application or implantation, or a combination of methods. Stabilization can enhance one or more of the durability, shelf life, and fatigue life of a bioprosthesis. Exemplary means of stabilizing a bioprosthesis include cross-linking components (e.g. proteins) of a tissue, inhibiting calcification associated with the tissue or the bioprosthesis incorporating the tissue, and/or co-incorporating a beneficial agent into the tissue or the bioprosthesis, including endogenous components of a natural tissue as well as exogenous components added to a tissue.

DESCRIPTION

In general, the present disclosure is directed to methods for improving the structural and mechanical characteristics of implantable tissue as well as methods for increasing the lifespan of implantable tissues. The disclosure is also directed to implantable tissues formed according to the disclosed methods. More specifically, the disclosed methods can include the bonding of one or more enzyme inhibitors in or on tissue in the course of a stabilization process. Through the disclosed methods, implantable tissues can be stabilized and can exhibit increased resistance to degradation, and specifically, degradation due to enzyme activity following implantation of the tissues. Disclosed methods can lead to increased levels of beneficial extra cellular matrix components remaining in the stabilized implantable tissues as compared to previously known stabilized implantable tissues. Increased levels of such components can further improve the implantable tissues through improved mechanical characteristics and can also lead to longer lifespan of a bioprosthesis.

Tissue as may be treated as disclosed herein can be derived from xenograft, allograft, or autologous tissue. Biological tissue can be harvested from an animal (e.g. a human, a cow, a pig, etc.). Disclosed methods can also be utilized in stabilizing synthetic tissues such as tissue engineered constructs. In general, suitable starting materials can be provided according to tissue culture techniques as are generally known in the art, and thus, such techniques are not discussed in detail herein. When considering natural sources for tissues as may be treated as disclosed herein, any suitable biological tissue can be utilized including, without limitation, heart valve, aortic root, aortic wall, aortic leaflet, pericardial tissue, connective tissue, dura mater, tendon, ligament, dermal tissue, blood vessel, umbilical tissue, fascia, submucosal tissue, and the like.

Specific enzyme inhibitors that can be included in an implantable tissue can depend upon the other components in the fixed tissue, both endogenous and exogenous components, as well as the specific application of the tissue, e.g., the implant environment. Similarly, preferred methods for binding any particular enzyme inhibitor in a tissue can depend upon the particular chemistry of the materials involved. In general, the enzyme inhibitor will be a non-endogenous component of the tissue.

For instance, in one preferred embodiment, a stabilization protocol can include the addition of a glycosaminoglycans degrading enzyme (GAGase) inhibitor to a tissue. Glycosaminoglycans (GAGs) are long unbranched polysaccharides that can act as a shock absorber or cushioning agent in a tissue present in the middle spongiosa layer of many tissues suitable for forming implants. According to this embodiment, one or more GAGs as may be found in an implantable tissue can be stabilized through the binding in the tissue of a compound that can inhibit enzyme(s) that hydrolyze or otherwise cleave the GAG(s). Moreover, GAGs that can be stabilized in and on the bioprosthesis can be either endogenous or exogenous. Typical GAGs as may be stabilized according to the present treatment methods can include, for example, hyaluronic acid (also known as hyaluronan and hyaluronate), chondroitin sulphate, keratan sulphate, dermatan sulphate, heparan sulphate, and the like.

Methods for stabilizing a portion of endogenous GAG present in tissue through binding of GAGS to tissue components have been previously disclosed. Exemplary GAG-stabilizing reagents include carbodiimides such as 1-ethyl-3-(3 dimethyl-aminopropyl) carbodiimide (EDC), heterofunctional azides, carbohydrate-protein linking reagents, and the like that can crosslink or otherwise bind GAGS within a fixed tissue. Unfortunately, such stabilization protocols bind only a limited amount of the endogenous GAGS of fixed tissue. In addition, previously known GAG stabilization protocols, while providing improved implantable tissues, do not prevent GAGase-mediated GAG loss in vivo. Accordingly, the present disclosure includes methods for binding a GAGase inhibitor in a tissue during a stabilization protocol.

In general, any GAGase inhibitor can be incorporated into a fixed tissue according to the presently disclosed methods. For example, sulfated oligosaccharides including sulfated verbascose, planteose and neomycin can be incorporated into a tissue. Apigenin, a flavone and known hyaluronidase inhibitor can also be utilized. Ascorbic acid 6 pharmatate, tetradecyl sodium sulphate, indomethacin, hesperidin phosphate, sodium aurothiomalate and glycyrrhizin are other known hyaluronidase inhibitors that can be utilized.

In one preferred embodiment, the GAGase inhibitor neomycin can be incorporated into an implantable tissue. Neomycin's chemical structure as shown:

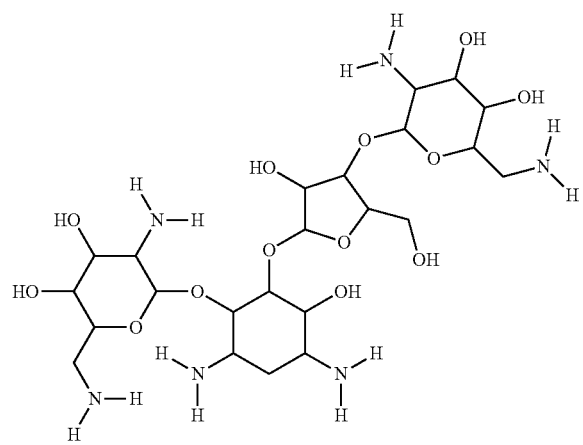

includes a plurality of free amines. Neomycin has been found to be effective as an enzyme inhibitor, particularly when in the salt form of the compound. Accordingly, a sulfate salt of neomycin can be incorporated into a fixed tissue in one preferred embodiment. For instance, a neomycin (e.g. a neomycin sulfate salt) can be covalently bound in an implantable tissue via reaction of a free amine group of the neomycin with an activated carboxyl group of another tissue component, for instance an endogenous tissue component such as collagen or GAGS, generally following activation of a carboxyl group of the tissue component with a suitable reagent such as EDC.

Neomycin includes multiple free amines and as such, multiple amide bonds can be formed between a single neomycin molecule and other components of a tissue. Accordingly, the addition of neomycin to a tissue during a stabilization process can not only provide enzyme inhibition activity to the tissue following implant, but can also provide crosslinking activity during the treatment protocol and can increase the amount of carboxyl-containing tissue components, and specifically, collagen and GAGS, in the implantable tissue. Additional crosslinking using other stabilizing materials, such as EDC/NHS crosslinking regimes discussed herein, can be used in conjunction with neomycin or other enzyme inhibitors to provide a stable, crosslinked tissue.

Methods and reagents suitable for safely binding other amine-containing materials in implantable tissues have previously been developed for protocols such as glutaraldehyde crosslinking and GAG stabilization. Such protocols previously developed for binding other amine-containing materials in implantable tissues can likewise be utilized in binding amine-containing GAGase inhibitors such as neomycin in an implantable tissue. Accordingly, the disclosed methods can be utilized to improve implantable tissues and can do so by using reagents that have been found safe and effective for use with other, previously known implantable tissues and devices.

Specific methodology for incorporating an enzyme inhibitor into an implantable tissue is not limited to such protocols, however. Any suitable system or method can be utilized in binding an enzyme inhibitor in a tissue during a stabilization process. For instance, epoxy reagents, heterobifunctional reagents, and the like, can be utilized. Common heterobifunctional crosslinkers suitable for use include, without limitation, those having an amine-reactive succinimidyl ester (i.e., NHS-ester) at one terminus and a sulfhydryl reactive group at another terminus. The sulfhydryl-reactive groups can be, for example, maleimides, pyridyl disulfides or α-haloacetyls. Suitable heterobifunctional reagents can also have one reactive group that is photoreactive rather than thermoreactive.

It should be understood that the present disclosure is not limited to neomycin GAGase inhibitors. For example, in one embodiment, heparin, which is a hyaluronidase inhibitor (see, e.g., Am J. Cardiol. 1984 Mar. 15; 53(7):941-4) can be bound in a tissue with or without additional enzyme inhibitors. Moreover, the disclosed subject matter is not limited to GAGase inhibitors. Other enzyme inhibitors can be bound within a stabilized tissue, including, without limitation, enzyme inhibitors with activity toward proteases (e.g., collagenase, elastase, matrix metalloproteinases (MMP's) and the like). In general, enzyme inhibitors that can be bound in a stabilized tissue can include, without limitation, enzyme inhibitors with carboxyl, hydroxyl or amine functionalities. For example, elastase inhibitors such as SSR69071, 1,4-bisphenyl-1,4-dihydropyridine derivates can be incorporated into a tissue. Examples of MMP inhibitors that can be included can be, without limitation, batimastat, marimastat, prinomastat, metastat and neovastat.

In addition to binding one or more enzyme inhibitors in or on a tissue, a treatment protocol for stabilizing an implantable tissue according to the present disclosure can include one or more additional aspects. For instance, a treatment protocol can include cross-linking proteinaceous or other components of a tissue. A crosslinking reaction can be carried out simultaneously or sequentially (in any order) with an enzyme inhibitor binding process.

Any methods and materials useful for cross-linking proteinaceous components of an implantable tissue can be used in the disclosed processes. For example, glutaraldehyde fixation of a biomaterial, particularly xenograft and allograft biomaterial, as is known to those of skill in the art, can be used. Glutaraldehyde fixation forms covalent cross-links between free amines in the tissue proteins. As a result, the tissue can be less susceptible to adverse immune reactions following implantation. Unfortunately, tissues that have been chemically fixed with glutaraldehyde are stiffer and less pliable than the native tissue. As a consequence of the increased stiffness, motion of the tissue during use can lead to material fatigue of the bioprosthetic. Moreover, in the specific case of cardiac implants, the recipient's heart will be required to work harder to overcome the stiffness of the bioprosthetic. As the material integrity of the implant is lessened over time, the efficiency of the implant operation decreases. Additionally, fatigue and mechanical degradation of the implant has been associated with increased calcification of the implant. The calcification causes additional stiffening which further degrades the physical and biological integrity of the implant.

Accordingly, the disclosed methods can include stabilization protocols that can be carried out in addition to glutaraldehyde fixation (either concordantly or sequentially therewith), or alternative to glutaraldehyde fixation protocols. For instance, in one embodiment, the elastin component of a tissue can be crosslinked through utilization of a phenolic tannin agent as disclosed in U.S. Patent Application Publication No. 2004/0153145 to Simionescu, et al., previously incorporated herein by reference. Phenolic tannins can interact with elastin as well as other connective tissue components. For instance, phenolic tannins can bind GAG and other connective tissue components not amenable for glutaraldehyde fixation. Specifically, phenolic tannins are understood to interact with elastin through proline-rich areas within the elastin matrix molecules. Tissue fixation protocols including treatment with a phenolic tannin reagent can not only improve the pliability and elasticity of a tissue as well as the strength and durability of the tissue, but can also provide a process for utilizing high elastin-content tissue in a bioprosthesis.

Treatment protocols as described herein can also include the stabilization of non-proteinaceous components of an implantable tissue as well as binding of additional beneficial components in or on a stabilized tissue. Component can be either exogenous or endogenous components. For instance, a treatment protocol can include GAG stabilization through crosslinking of the GAGS, as discussed above. Other components that can be included in an implantable tissue via covalent binding, ionic binding, hydrogen bonding, or any other incorporation method can include, without limitation, polyepoxy amine compounds, buffering agents, physiological salts, calcification inhibitors, and the like.

For instance, previous research has suggested that ethanol pretreatment and pre-incubation before implantation has reduced calcification greatly. Accordingly, in one embodiment, disclosed stabilization protocols can include an ethanol treatment regime, as is generally known in the art.

Beneficially, it has been found that the inclusion of a GAGase inhibitor such as neomycin in a stabilized tissue can not only provide good stabilization of GAGs against GAG-degrading enzymes, but can also provide good stabilization of collagen and elastin against enzymes that are known to degrade these proteins, e.g., collagenase and elastase. Accordingly, disclosed methods can be beneficial in preparing stentless valves that tend to include a proportionally large amount of aortic tissue, which contains more elastin and collagen than other tissues often utilized in forming other types of valves.

Due to the maintenance of beneficial extracellular matrix components in disclosed stabilized tissue, the mechanical characteristics of the tissues can be maintained. For instance, valvular tissue buckling has been implicated in the evolution of fatigue failure in bioprostheses. Characterized by structural deformations, buckling occurs at areas of large stresses during valvular motion (see, e.g., FIG. 10). During diastole, xenograft valves are subjected to uniaxial compression due to sharp bending in the belly and commissural regions of the cusps. Such valvular behavior produces surface kinks and crimps, resulting in local structural collapse to reduce the bending stresses. Upon initiation of buckling, such tissue-bending deformations continue to occur in the same area during each successive valvular cycle. Consequentially, the bending site fatigues, which may lead to subsequent tearing of the cusp. By modulating shear stresses, medial spongiosa layers of stabilized tissues formed as described herein that can be rich in GAGs, can buffer the appositional movement of the outer layers in valves, which are subjected to tensile and compressive loads. These hydrophilic GAGs can form a gel-like layer capable of absorbing such stresses during valvular bending.

As previously mentioned, previously known chemical stabilization of valvular GAGs does not prevent enzymatic degradation of these extracellular matrix components, as the carboxylic acid functionalities of GAGs are active sites for enzymatic degradation. Thus, previously known GAG stabilization methods such as carbodiimide crosslinking might have prevented enzyme binding to some carboxyl groups in GAGs, but as all carboxylic acids are not involved in crosslinking, enzymes could still cleave GAGs. Utilizing presently disclosed stabilization methods, which can be, in one embodiment, coupled with carbodiimide-based crosslinking chemistry, valvular cusps can inhibit enzyme-mediated GAG degradation, as the enzyme inhibitor compound can not only block active sites on GAGs but can also inactivate GAG-digestive enzymes by binding thereto. Steric hindrance of active sites and conformational change of the enzymes can prevent loss and digestion of GAGs.

Stabilization of tissue GAGs in implantable tissue that can be subject to a great deal of motion following implantation, such as tissue intended for use in a heart valve, for instance, can extend the expected lifespan of the implant. During the cardiac cycle, valvular cusps are continuously subjected to tensile, compressive, and shear stresses. The interlayer shearing between the fibrosa and ventricularis is mediated by the medial spongiosa layer. GAGs of the tissue, hydrophilic in nature, form a gel-like layer in the spongiosa capable of distributing and dissipating these valvular stresses. Stabilization of the native GAGs of the tissue as described herein can maintain this layer throughout the life of the implant. Interestingly, and as described in more length below, tissues treated as described herein can demonstrate no difference in buckling behavior after accelerated fatigue testing as compared to buckling patterns of statically stored tissues. Additionally, GAG-stabilized tissue as described herein can exhibit minimal fractional depth of buckling compared to glutaraldehyde-crosslinked tissue.

The inclusion of one or more enzyme inhibitors as described herein can be combined with other tissue stabilization methods as are generally known in the art. For instance, combined use of a GAG-stabilizing reagent and a polyepoxy amine compound to treat an implantable bioprosthetic device can enhance stabilization of the bioprosthesis relative to treatment with the polyepoxy amine compound alone. Accordingly, the disclosed subject matter encompasses the inclusion of a polyepoxy amine compound in a fixation protocol according to known methods in combination with the binding of one or more enzyme inhibitors in or one the tissue, either simultaneously or sequentially in either order, for stabilization of a bioprosthetic tissue.

A stabilized tissue of the present disclosure can generally be utilized in any implantable bioprosthesis. For instance, the disclosure encompasses any of a variety of cardiac bioprostheses that can replace or support damaged sections of the cardiovascular system. For example, bioprosthetic heart valves, veins, or arteries are encompassed as well as other bioprostheses previously mentioned.

A bioprosthesis can include stabilized implantable tissue as herein disclosed in conjunction with other implantable support materials as are generally known in the art. For instance, a bioprosthesis can include disclosed implantable tissue in suitable combination with support materials such as forms, stents, suture rings, conduits, flanges, and the like.

In one embodiment, a bioprosthetic heart valve (BPHV) can be formed including heart valve leaflets formed of fixed biomaterials as disclosed herein secured to a stent. Suitable stent materials can generally include stent materials as may generally be found in other known heart valves, including both mechanical and bioprosthetic heart valves. For example, tissue leaflets can be attached to a flexible polymer stent formed of, for instance, polypropylene reinforced with a metal ring (such as, for example, a Haynes™ alloy no. 25 metal ring). Polymeric stents are also known, such as a polymer stent including a polyester film support secured to a surgically acceptable metal ring such as an Elgiloy™ metal stiffener.

Optionally, a support material may be formed of only polymeric materials, and not include any metals. Alternatively, the disclosed bioprosthesis can include a metal support, e.g., a wire stent, such as an Elgiloy™ wire stent, or a titanium stent, which can be optionally covered with a cover, such as, for example, a fabric cover such as a Dacron™ fabric. In one embodiments, a bioprosthesis, e.g., an implantable BPHV, can include a sewing or suture ring such as, for example, a polyester, Dacron™, or Teflon™ suture ring, as is generally known in the art. In yet another embodiment, a disclosed implantable tissue can form a stentless heart valve. The specific make-up of any support material in a disclosed bioprosthesis is not critical to the disclosed subject matter.

Following formation of a bioprosthetic device, e.g., a BPHV, the device can be implanted by any surgical procedure as is generally known in the art. For example, a BPHV including a stabilized tissue can be implanted in the heart of a person or an animal according to known surgical procedures such as, for example, procedures described in U.S. Pat. No. 6,532,388 to Hill, et al., U.S. Pat. No. 6,506,197 to Rollero, et al., and U.S. Pat. Nos. 6,402,780, 6,042,607, and 5,716,370 all to Williamson, IV, et al., all of which are incorporated herein by reference. In general, such procedures include removal of a damaged cardiac valve, implantation of the new replacement valve in the cardiac valve annulus, and attachment of the BPHV to the adjacent tissue.

Reference now will be made to exemplary embodiments set forth below. Each example is provided by way of explanation of the disclosure, not as a limitation.

Example 1

Methods

Porcine heart valve were obtained from an abattoir. They were dissected along the cuspal commissures. The cusps were left attached to the aortic sinus at the basal insertion to minimize GAG loss from the cusps. The cusps were rinsed three times in cold saline and were divided into three groups (12 cusps per group). The three groups were treated within three to four hours of harvesting with stabilization reagents as follows:

Group 1—(Neomycin trisulfate+EDC+Glut). Cusps were treated via agitation at room temperature in a solution of 1 mM Neomycin at pH 7.4 for 1 hour. The cusps were then rinsed with deionized water followed by fixation in a solution including 30 mM 1-ethyl-3-(3-dimethylaminopropyl) carbodiimide (EDC) and 6 mM n-hydroxy succinimide (NHS) buffered with 50 mM 4-morpholinoethanesulfonic acid (MES) hydrate at a pH of 5.5 for 24 hours at room temperature. The cusps were then rinsed with deionized water. This was followed by fixing in 0.6% glutaraldehyde 50 mM 4-(2-hydroxyethyl)-1-piperazineethanesulfonic acid (HEPES) at pH 7.4 at room temperature for 24 hours followed by additional fixing in 0.2% glutaraldehyde in HEPES buffer at pH 7.4 for 6 days.

Group 2—(EDC+Glut). Cusps were fixed in a solution including 30 mM EDC and 6 mM NHS buffered with 50 mM MES hydrate at a pH of 5.5 for 24 hours at room temperature. The cusps were then rinsed with deionized water. This was followed by fixing in 0.6% glutaraldehyde 50 mM HEPES at pH 7.4 at room temperature for 24 hours followed by additional fixing in 0.2% glutaraldehyde in HEPES buffer at 7.4 for 6 days.

Group 3—Glutaraldehyde (Control). The cusps were fixed in 0.6% glutaraldehyde 50 mM HEPES at pH 7.4 at room temperature for 24 hours followed by additional fixing in 0.2% glutaraldehyde in HEPES buffer at 7.4 for 6 days.

Cusps in all groups were stored in 0.2% glutaraldehyde further as per study design.

In order to study GAG stability to enzymes, cusps were incubated in a solution containing 10 U/ml hyaluronidase and 0.2 U/ml chondroitinase for 24 hours. Hexosamine assay was then performed on the cusps. GAGs that leached into the solution due to enzyme degradation were quantified using dimethyl methylene blue (DMMB) assay. These two assays were complimentary to verify and cross check the results.

Hexosamine content of cusps fixed in each of the three different groups, incubated in the GAG degrading enzymes, and then stored in 0.2% glutaraldehyde for 1, 4, 6, and 12 months of storage are shown in FIGS. 1A to 1D, respectively. The cusps of Group 1 (Neomycin trisulfate+EDC+Glut) showed enhanced GAG stability compared to the cusps of Group 2 (EDC+Glut) and those of Group 3 (Glut). Cusps of Groups 2 and 3 lost GAGs during crosslinking as suggested by the data for undigested cusps (left bars). After enzyme digestion, glutaraldehyde-crosslinked tissue of Group 3 lost most of the GAGs while the Neomycin group (Group 1) showed no loss of GAGs. This suggests that neomycin covalently linked to the tissue acts as GAGase inhibitor thereby providing improved stabilization of GAGs present in the tissue. It is clear that the cusps of Group 3 progressively lose GAGs initially present in the tissue. The cusps of Group 1 show no statistical difference or loss of GAGs following one year of storage.

Figure 2:
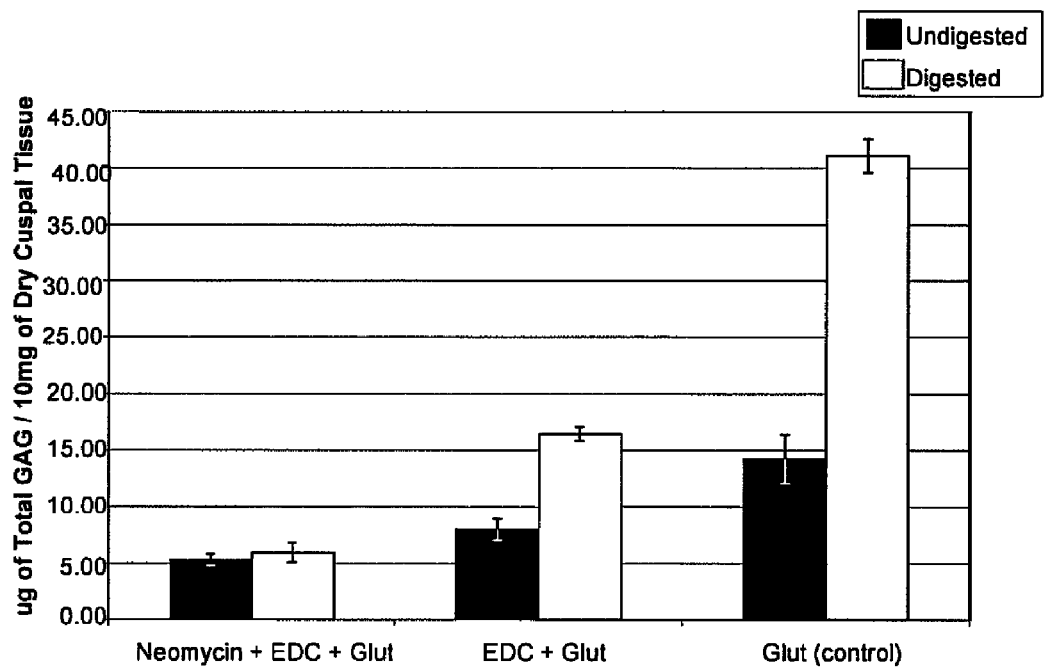
FIG. 2 is a graph setting forth the hexosamine content in enzyme/buffer solutions used in enzyme digestion of the cuspal tissues of FIG. 1A as determined via DMMB assay.

In order to verify the GAG loss, DMMB assay was performed on the enzyme/buffer solutions used for enzyme digestion. Results are shown in FIG. 2. Enzyme and buffer solutions for cusps crosslinked with glutaraldehyde only (Group 3) showed the highest amount of total GAGs, thus confirming results obtained for cusp tissue. Only baseline GAG content was seen in enzyme and buffer solutions for the Group 1 cusps (Neomycin trisulfate+EDC+Glut), again showing excellent resistance of the cusps of Group 1 to enzyme mediated degradation.

Figure 3A:
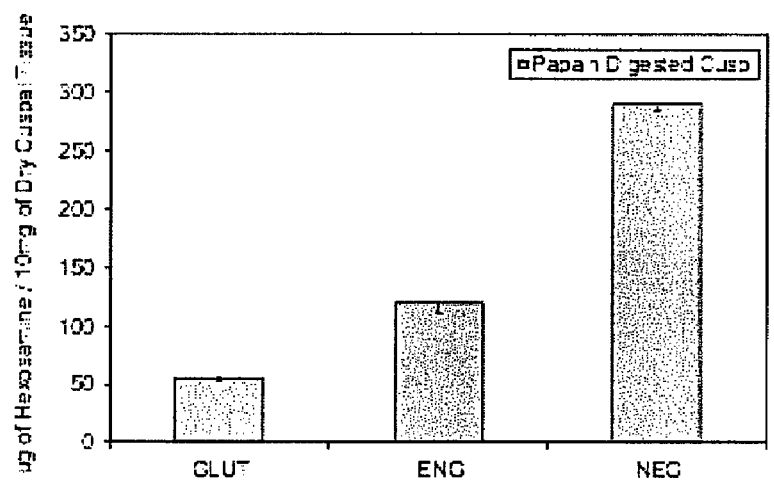
FIG. 3 illustrates the GAG retention of tissues treated as described herein following papain digestion as described by hexosamine assay (FIG. 3A) and DMMB assay of the papain solution (FIG. 3B).
Figure 3B:
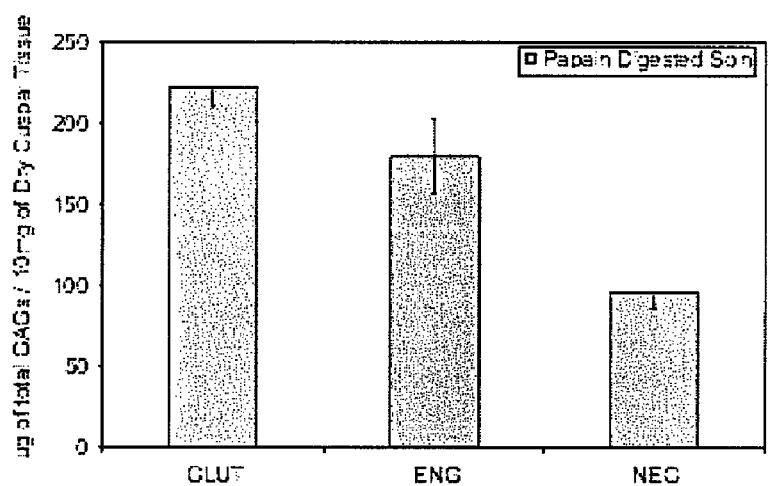

To further test the stability of crosslinked GAGs against enzymes, cusps were treated with papain. Following papain digestion, cusps were examined via the hexosamine assay. Results are shown in FIG. 3. As can be seen, the cusps in Group 1 (Neomycin trisulfate+EDC+Glut) retained most GAGs after papain digestion, followed by Group 2 (EDC+Glut) ($p<0.05$). The Group 3 cusps shown the least resistance to papain digestion and retained the least amount of GAGs (FIG. 3A). The amount of degraded GAGs released into the papain solution was analyzed using DMMB assay. Cusps from Group 1 released the least amount of GAGs into the papain digestion buffer (FIG. 3B).

Figure 4:
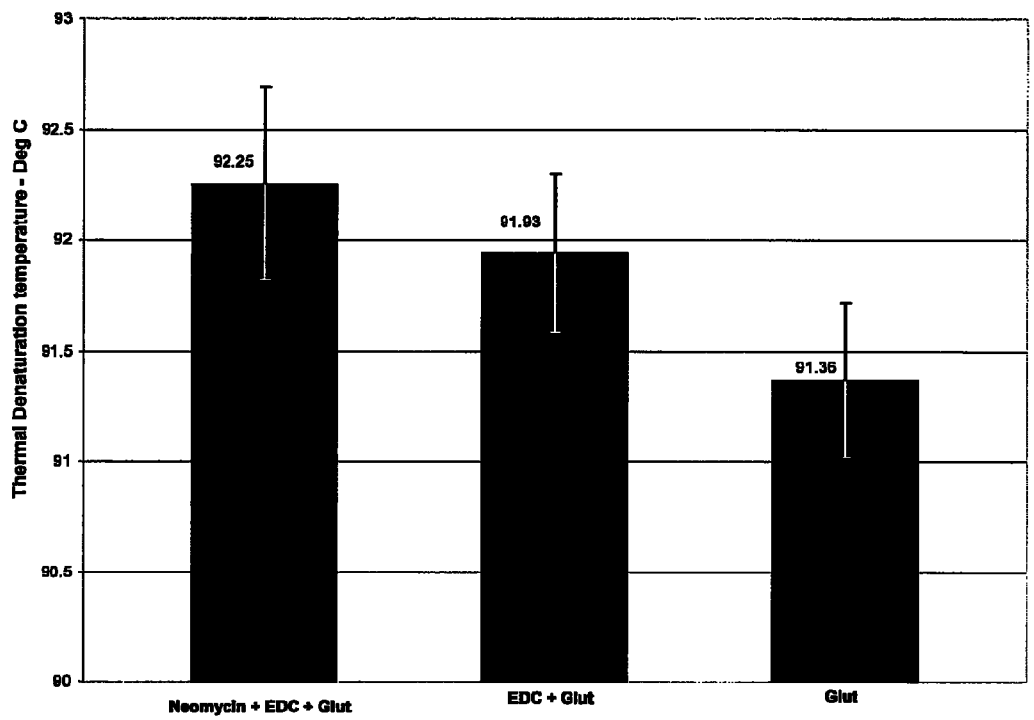
FIG. 4 is a graph setting forth the thermal denaturation temperatures ($T_d$) obtained by differential scanning calorimetry (DSC) for cuspal tissues treated according to one of three different fixation regimes.

To make sure that neomycin binding did not affect the collagen crosslinking, DSC analysis was performed for thermal denaturation temperature ($T_d$) of collagen. FIG. 4 shows that the binding of neomycin did not reduce $T_d$ of cusps, suggesting that binding of neomycin did not affect collagen crosslinking. $T_d$ values were similar for all groups (Group 1: 92.26±0.43° C., Group 2: 91.94±0.36° C., Group 3: 91.37±0.35° C., $p<0.05$). This can be important for many bioprostheses, for example as $T_d$ values above 90° C. are favored for heart valve bioprostheses.

Figure 5:
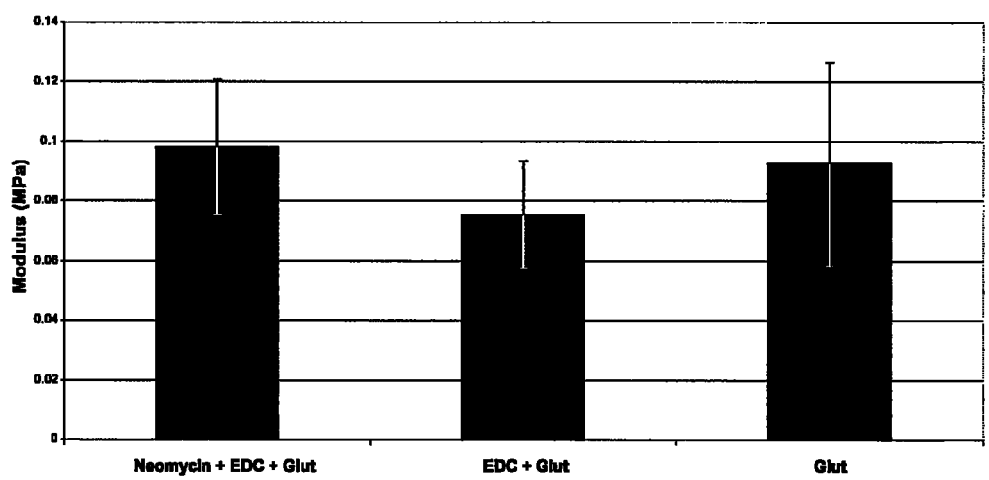
FIG. 5 is a graph setting forth the modulus of cuspal tissues fixed according to one of three different fixation regimes.

Compression testing was done on the treated cusps by removing a round section from the center of the cusps. The thickness of the cusps was measured and the crosshead speed of the testing device was set to 5% of the thickness. The testing was done in saline. Results are shown in FIG. 5. Similar compression modulus values were seen for glutaraldehyde-crosslinked and neomycin-treated groups suggesting that binding of neomycin did not affect compression properties of treated tissue.

Example 2

Cusps from each of the three treatment groups described above in Example 1 were subdermally implanted in Sprague Dawley juvenile male rats. Prior to implantation, GAG values were determined for all groups. Samples were explanted after 3 weeks and analyzed for hexosamine and calcium content.

Figure 6:
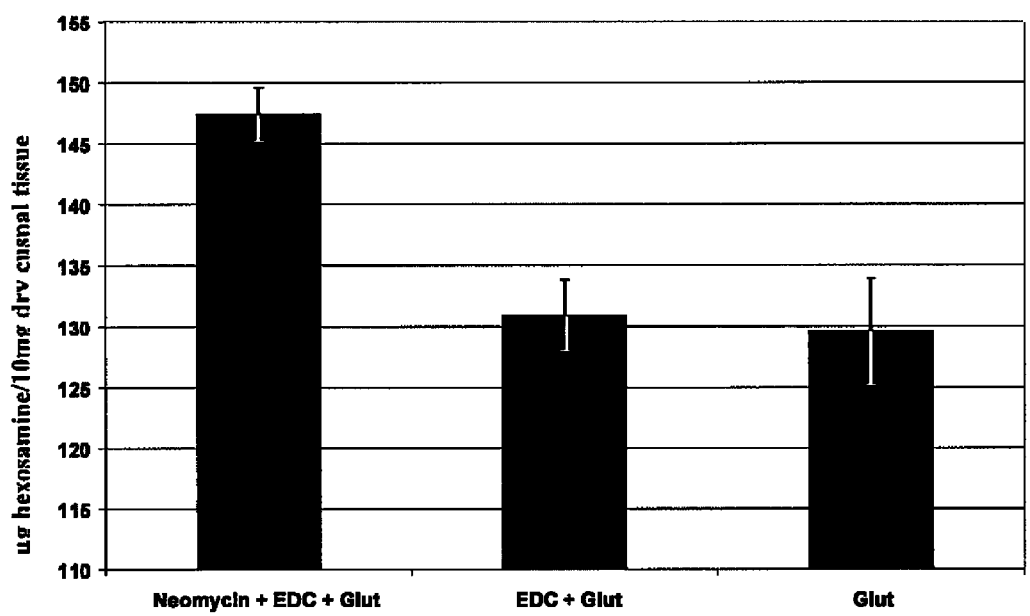
FIG. 6 is a graph setting forth the results of a hexosamine assay of cuspal tissues fixed according to one of three different fixation regimes followed by in vivo implantation.

Results of hexosamine analysis of the explanted samples are shown in FIG. 6. As can be seen, the neomycin group (Group 1) had statistically more hexosamine than other groups. After explantation, Group 1 showed maximum retention of cuspal GAGs as compared to the other two groups. Glutaraldehyde crosslinking alone was found to be ineffective in crosslinking GAGs.

Figure 7:
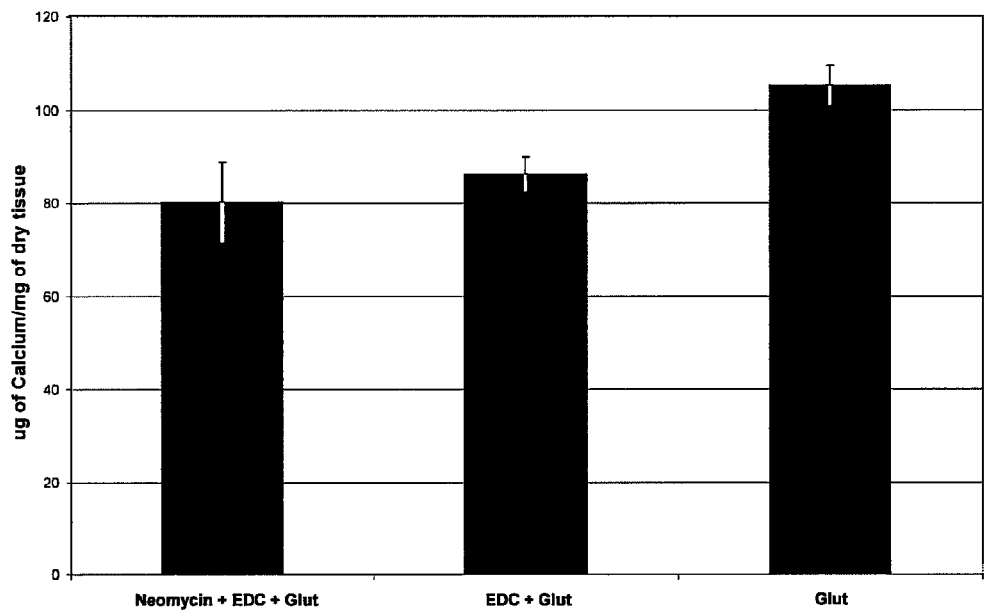
FIG. 7 is a graph setting forth the results of a calcium assay on the explanted tissues of FIG. 6.

Calcification in the explanted cusps was also determined by performing a calcium assay on the explanted samples. Results are shown in FIG. 7. As can be seen, the neomycin group (Group 1) was found to have lower calcification as compared to Groups 2 and 3. However, the GAG stabilization did not lead to inhibition of calcification. As all groups were terminally fixed with glutaraldehyde, which is known to exacerbated calcification, it is possible that the glutaraldehyde effect was dominant in the calcification process.

Overall, the tissues of Group 1, including neomycin, showed enhanced GAG retention and stability against GAG degrading enzymes, as well as less calcification, than tissues treated only with currently used glutaraldehyde crosslinking methods.

Figure 8:
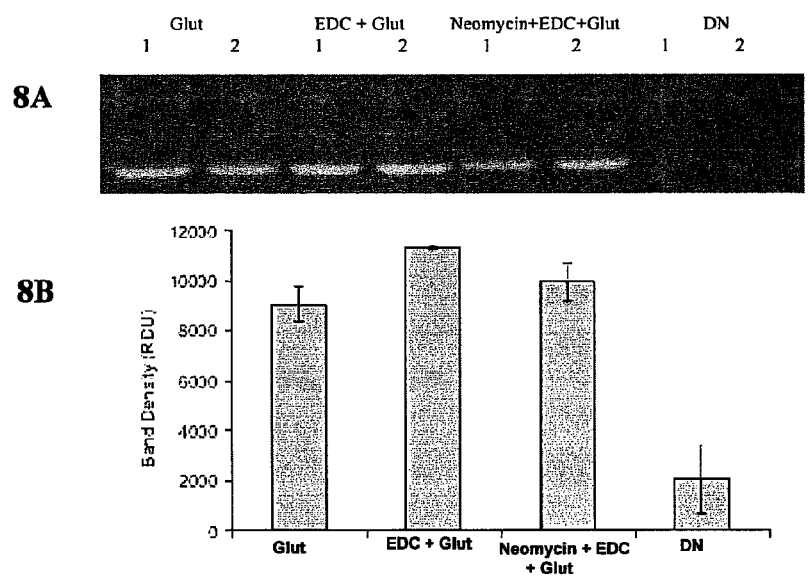
FIG. 8 illustrates hyaluronic acid zymography of explanted tissues treated as described herein including electrophoresis gel results (FIG. 8A) and graphical representation of the band density (FIG. 8B) for each sample type.

Hyaluronic acid zymography studies were performed to study the inhibitory effect of neomycin on hyaluronidase. Tissue capsules from 3 weeks explanted treated aortic cusp samples were homogenized and used for gel zymography. Hyaluronic acid (HA) gels were made by incorporating 170 μg/ml of HA in 10% polyacrylamide gels. The tissue extracts were run at 90 Volts for 150 minutes. Protein molecular weight standards (10-150 kDa) were used to identify the molecular weights. Gels were incubated in the developing buffer (two for each sample type) and gels were also incubated in developing buffer containing 1 M neomycin. FIG. 8a and FIG. 8B show similar band intensities for active hyaluronidases in all groups. Thus, presence of more GAGs in Group 1 (Neomycin+EDC+GLUT) was not due to lower enzyme activity in this group as compared to other groups. When neomycin trisulfate was added to the development buffer it inhibited enzyme activity (DN1 and DN2 lanes on FIG. 8A, DN on FIG. 8B). This depicts the inhibitory effect of neomycin on hyaluronidase and suggests that incorporation of neomycin trisulfate into cuspal structures could prevent enzyme-mediated degradation of GAGs in implants such as BHVs.

Example 3

Porcine aortic heart valves were obtained from a USDA-approved abattoir. Fresh porcine aortic heart valves were thoroughly rinsed in ice-cold saline. Within 3 hours of harvesting, intact aortic valves were stuffed with cotton to maintain diastolic morphology and chemically crosslinked in one of three fixation groups as follows:

Group 1: 1-hour incubation in 1 mM neomycin trisulfate solution comprised of MES buffer solution at a pH of 7.4. Following, valves were rinsed with deionized water and subsequently fixed with carbodiimide fixation chemistry with 30 mM EDC/6 mM NHS solution buffered with 50 mM MES hydrate at a pH of 5.5 for 24 hours at ambient temperature. Following the carbodiimide fixation, valves were thoroughly rinsed in a 50 mM HEPES buffered (pH 7.4) saline solution and subsequently crosslinked with 0.6% glutaraldehyde for 24 hours, followed by storage in 0.2% glutaraldehyde for 5 days.

Group 2: 30 mM EDC/6 mM NHS solution buffered with 50 mM MES hydrate at a pH of 5.5 for 24 hours at ambient temperature. Following the carbodiimide fixation, valves were thoroughly rinsed in a 50 mM HEPES buffered (pH 7.4) saline solution and subsequently crosslinked with 0.6% glutaraldehyde for 24 hours, followed by storage in 0.2% glutaraldehyde for 5 days.

Group 3: Valves were fixed in 0.6% Glutaraldehyde in 50 mM HEPES buffered saline solution at pH 7.4 at ambient temperature for 24 hours, followed by 0.2% Glutaraldehyde in 50 mM HEPES buffered saline solution at pH 7.4 for 6 days at ambient temperature.

Group 4: Fresh porcine aortic valves that were not chemically fixed were used as controls.

Following tissue fixation and storage procedures, cusps were excised from their subtending aortic walls and thoroughly rinsed in 100 mM ammonium acetate buffer (pH 7.4).

Whole cusps were incubated in 1.2 ml solution containing 10 U/ml high purity hyaluronidase and 0.2 U/ml high purity chondroitinase buffered in ammonium acetate buffer for 24 hours at 37° C. under vigorous shaking at 650 RPM. Following incubation in enzyme-buffered solutions, samples were thoroughly rinsed in deionized water.

Figure 9A:
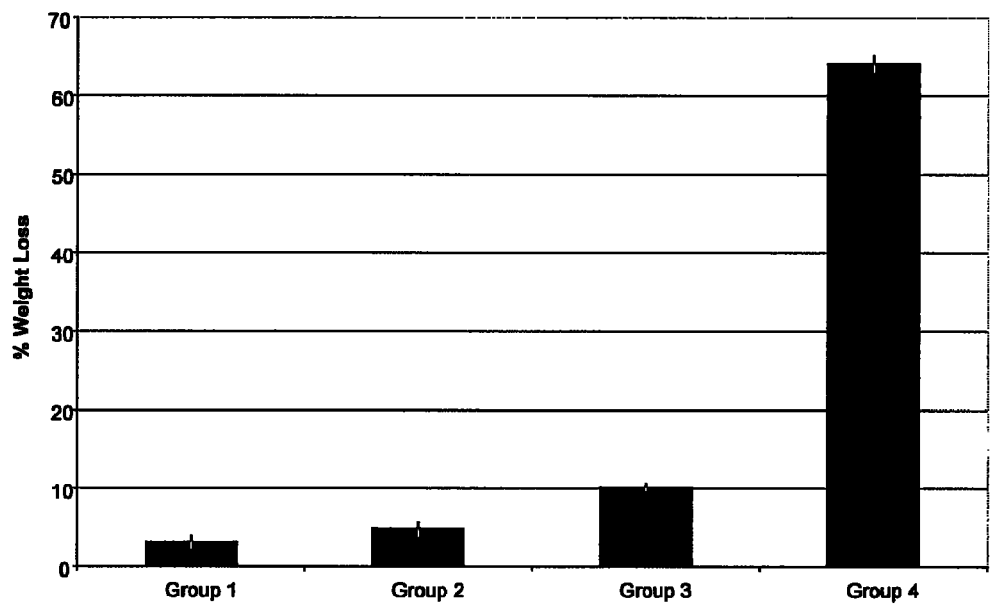
FIG. 9 illustrates cuspal weight loss data for cusps treated as described herein upon treatment with collagenase (FIG. 9A) and elastase (FIG. 9B)
Figure 9B:
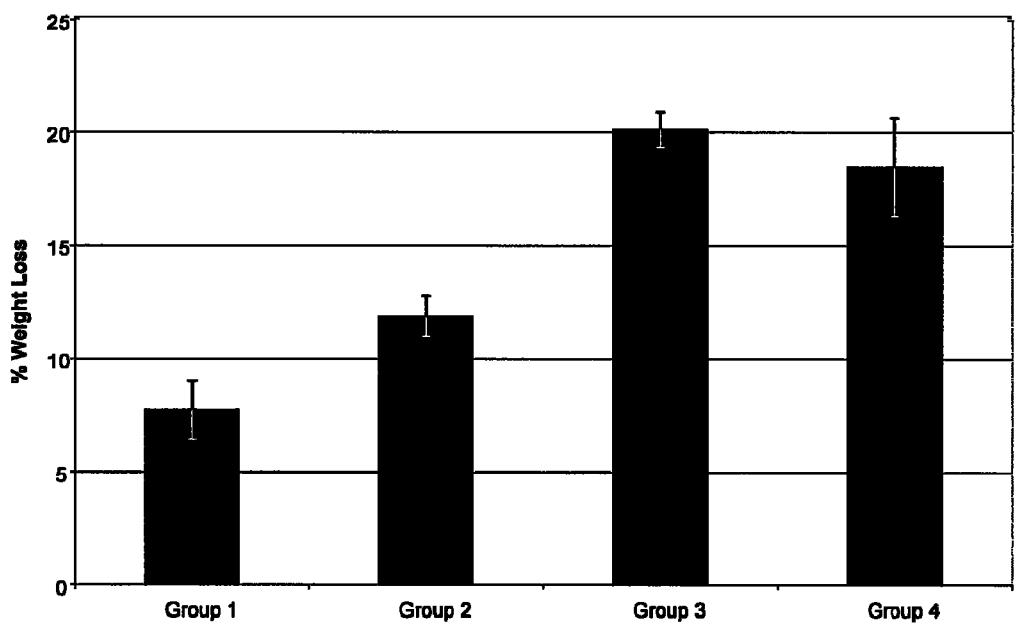

In order to determine the stability of cuspal tissue collagen and elastin, cusps were treated against collagenase and elastase and the corresponding weight loss data documented as shown in FIG. 9. As can be seen, fresh tissue lost a great deal of weight after treatment with collagenase compared to the 3 different fixed tissues (FIG. 9A). Glutaraldehyde was used terminally in all groups for fixation and is known to be an excellent collagenous fixative as it forms Schiff's base bonds with collagen and stabilizes collagen. In the case of tissue treated with elastase, it can be seen in FIG. 9B that there was a great deal of weight loss in all groups with Group 1 losing the least weight and Groups 3 and 4 losing the most weight.

To examine the potential role of GAGs in valvular tissue buckling, fresh untreated, glutaraldehyde-crosslinked, and GAG-stabilized cusps were subjected to varying radii of curvatures. Additionally, to observe buckling in GAG-depleted valvular tissue, these cusps were exposed to GAG-digestive enzymes prior to evaluation of tissue buckling pattern.

Specifically, cusps were excised from the aortic root, and circumferential strips were obtained from the belly region of the cuspal tissue. 5 mm wide strips (with varied length to fit the desired curvature) were bent to desired curvatures by bending them against natural curvature to mimic physiological bending in the belly region of the cusps. To maintain a bent configuration of the cusps, stainless steel pins were pierced through both ends of the strips; the ends were separated to a desired radius of curvature and held in place by using cork stoppers at either end of the pin for 24 hours in 0.2% Glut solution.

The radius of curvature was varied by changing the length of the tissue to satisfy the relationship:

$$s = r \cdot \theta_{radians}$$

Whereby s denotes the arc length of the curvature, r represents the desired radius of curvature, and $\theta_{radians}$ is the radian angle of the arc. In this case, a radian angle of 7 was used to represent a semi-circular arc produced by the bent cuspal strips.

Figure 10:
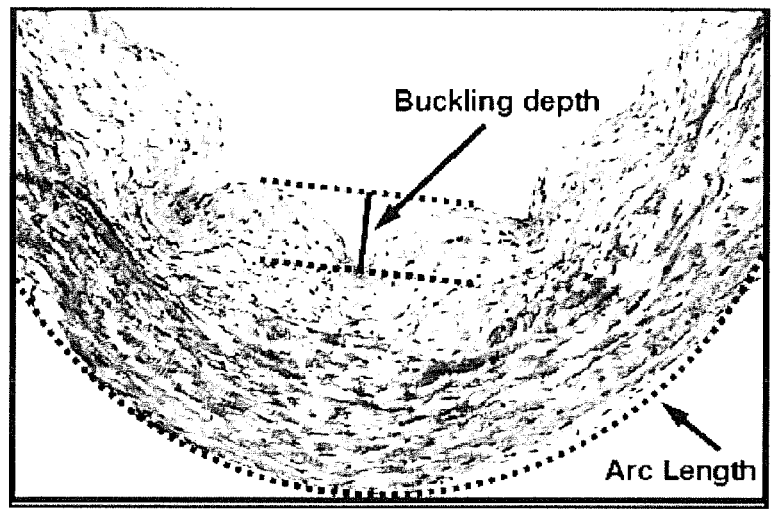
FIG. 10 illustrates tissue buckling quantification information.

The extent of buckling was quantified using a Zeiss Axioskop 2 plus (Carl Zeiss MicroImaging, Inc., Thornwood, N.Y.) in conjunction with SPOT Advanced software. Using measuring and drafting functions, such as circular and linear dimension line features of the SPOT Advanced software, the actual curvature of the bending, tissue thickness, and depth of buckling were measured. To determine the radius of curvature, a circle was fitted visually to the semi-circular arc of the tissue. The tissue thickness was measured by averaging the local thickness of the tissue away from the sites of tissue buckling. Depth of tissue buckling was quantified by measuring the distance between the deepest point of buckling and the inner boundary of the tissue thickness, as illustrated in FIG. 10. Depth of tissue buckling was quantified by measuring the distance between the deepest point of buckling and the inner boundary of the tissue thickness. Arc length was determined by fitting a circular function around the bending arc of the tissue. The fractional depth of buckling was obtained by dividing buckling depth by the local tissue thickness. Due to variability in tissue thicknesses among cusps, the bending curvature and tissue thickness were expressed as a product. Also, expressing these two independent variables as a product increased the correlation coefficients of the obtained graphical plots.

To normalize the variation in tissue thickness between samples, the curvature was multiplied by the local thickness of tissue. Thus, both variables, curvatures and tissue thickness, affect the degree of buckling depth. Per histological observations, it was evident that as the radius of curvature decreased, or as the curvature of bending increased, the extent of buckling increased. To demonstrate this relationship, fractional depth of buckling versus the product of tissue thickness and curvature of bending were plotted.

To assess the affect of chemical fixation on the number of buckles produced by valvular tissue bending, the number of buckles present in the semi-circular arc of bent cuspal strips was determined.

Figure 11:
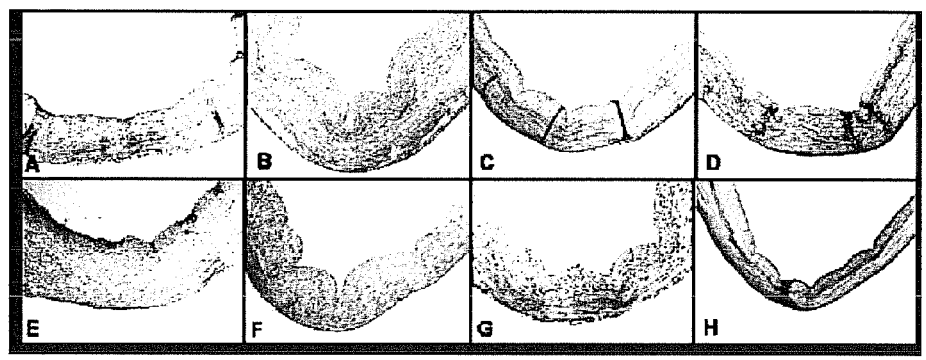
FIG. 11 provides histological evaluation of buckling behavior before and after exposure to GAG degrading enzymes for fresh untreated tissue (FIGS. 11A and 11E), for glutaraldehyde crosslinked tissue (FIGS. 11B and 11F), for carbodiimide crosslinked tissue (FIGS. 11C and 11G), and for cusps treated with neomycin trisulfate coupled with carbodiimide fixation (FIGS. 11D and 11H), all samples were bent to similar curvature (original magnifications ×100)

Histology results showed that the extent of buckling increased with decreasing radii of bending or with an increase in curvature. Of note, a greater depth of buckling in general was observed in cusps crosslinked with glutaraldehyde, compared to fresh, untreated cusps (FIGS. 11A and 11B). However, unlike glutaraldehyde-crosslinked cuspal tissue, cusps pretreated with GAG-targeted fixation chemistries exhibited only moderate tissue buckling (FIGS. 11C and 11D). After GAG digestion, only glutaraldehyde crosslinked cusps showed increased buckling (FIGS. 11E-H).

Figure 12C:
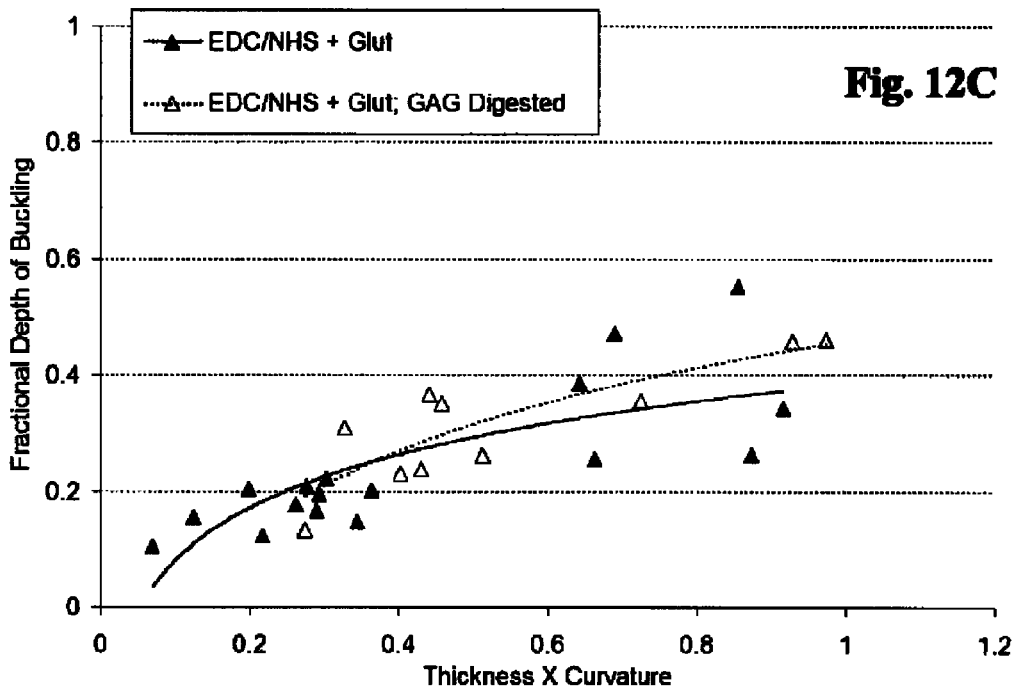
FIG. 12 provides graphical analyses of fractional depth of buckling of tissues illustrated in FIG. 11, with fractional depth of buckling plotted against the product of thickness and curvature.
Figure 12D:
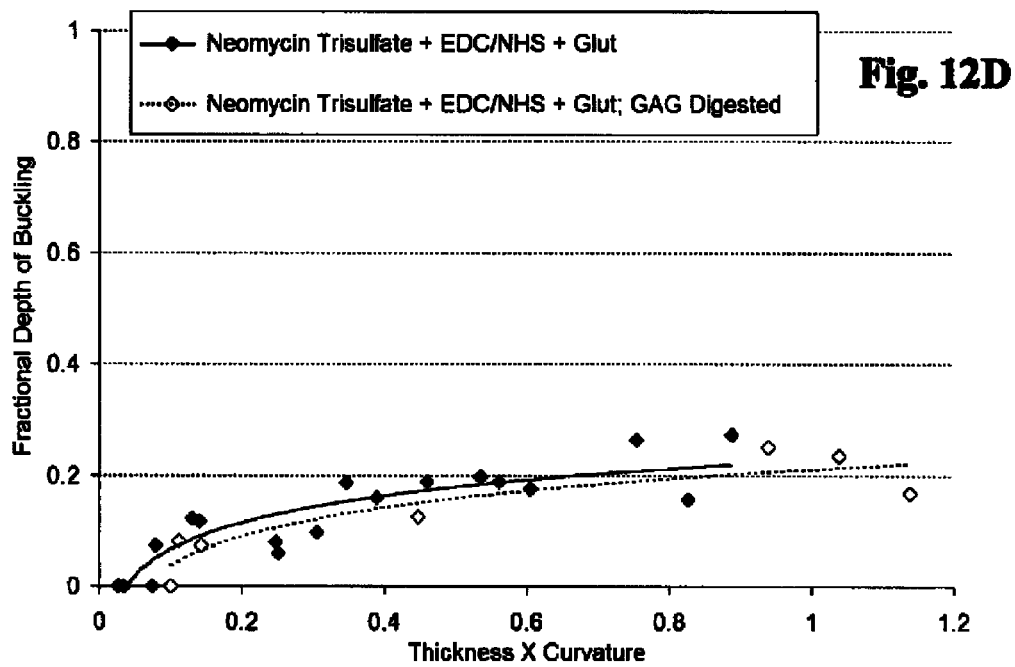

The fractional depth of buckling was plotted against the product of bending curvature and tissue thickness. The graphical analyses are shown in FIG. 12. Analysis suggests that fresh valvular cusps not exposed to any chemical pretreatment experienced relatively mild compressive buckling, with an absence of such tissue deformations at low curvatures. However, glutaraldehyde-crosslinked cusps experienced a greater depth of buckling at all curvatures, including mild bending curvatures ($p<0.05$) (FIGS. 12A and 12B). Moreover, when exposed to GAG-digestive enzymes, these glutaraldehyde-crosslinked cusps buckled almost through their entire thickness when tightly bent to high curvatures. Conversely, only slight increase in buckling pattern was observed in untreated, fresh cusps after treatment with GAG-degrading enzymes. Thus, at all bending radii, the fractional depth of buckling in fresh, untreated cusps was significantly lower than in cusps crosslinked with glutaraldehyde with or without GAG-digestion ($p<0.05$). At high curvatures, cusps treated with carbodiimide fixation chemistry alone buckled to a lower extent than those with glutaraldehyde-fixed cusps ($p<0.05$) (FIG. 12C). Cusps with bound neomycin trisulfate experienced the least degree of buckling at all bending curvatures than their glutaraldehyde-crosslinked counterparts bent to similar configurations ($p<0.05$) (FIG. 12D). Moreover, following GAG-digestion treatment, neomycin trisulfate treated tissues exhibited no significant difference in buckling pattern ($p>0.05$) (FIG. 12D).

Figure 13A:
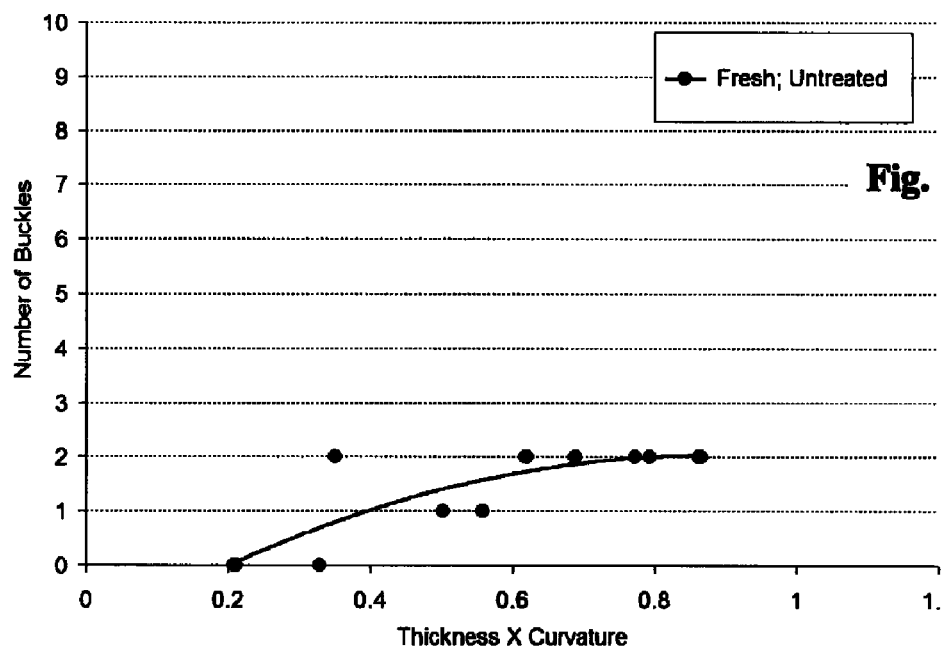
FIG. 13 provides graphical evaluation of change in number of buckles of tissues illustrated in FIG. 11, with number of buckles plotted against the product of thickness and curvature.
Figure 13B:
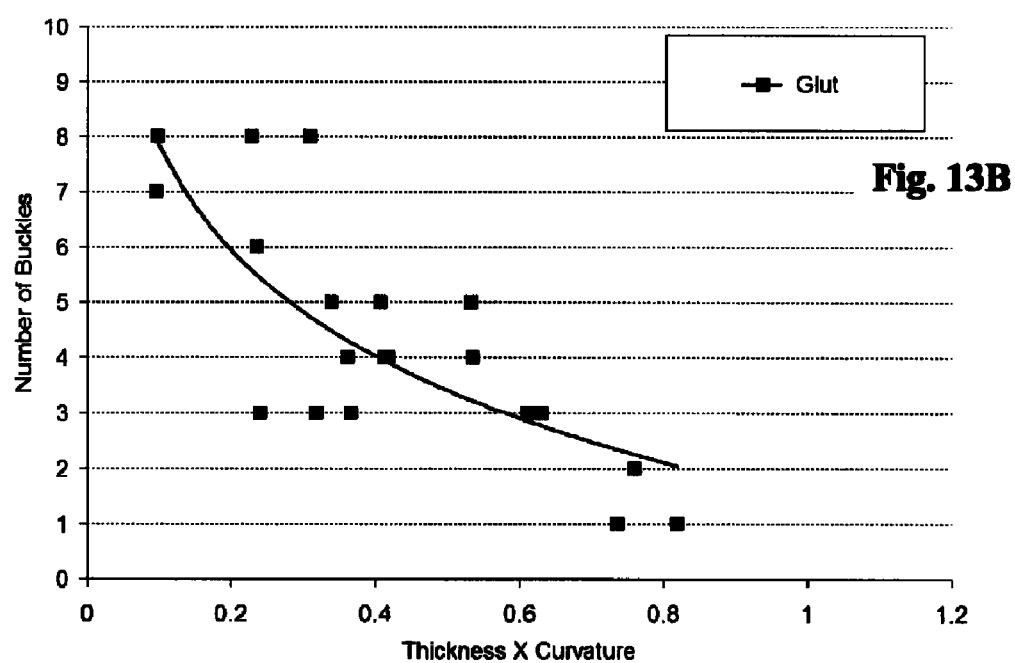
Figure 13C:
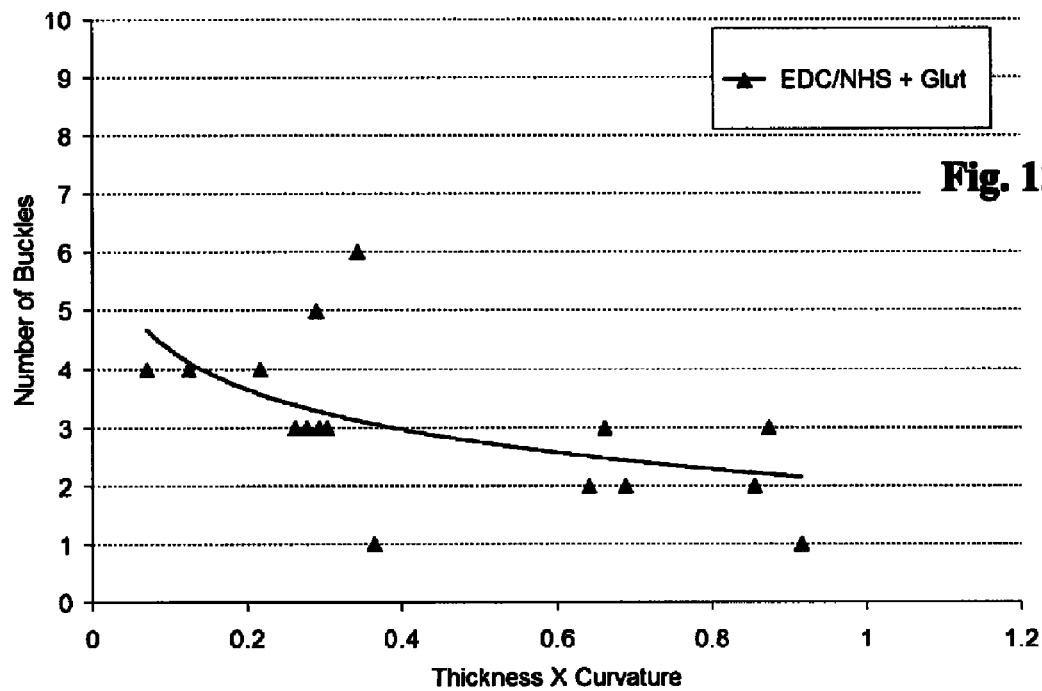
Figure 13D:
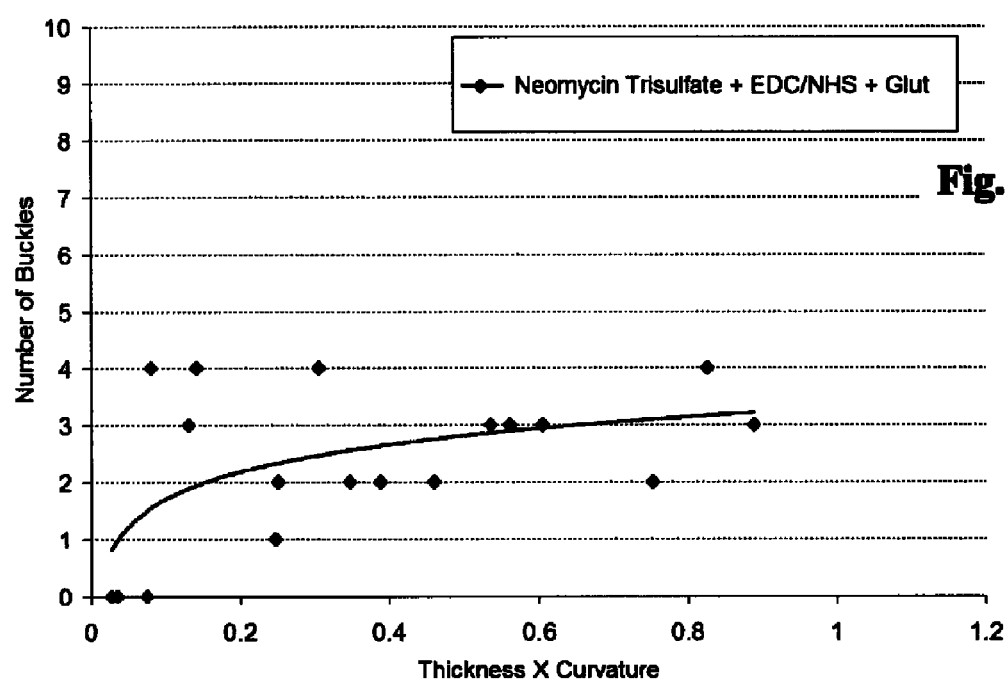

To further characterize the surface buckling pattern of the treatment groups, the number of buckles developed during various cuspal bending radii was quantified. Results are graphically illustrated in FIG. 13. Fresh, untreated cusps experienced no buckling at low curvatures (FIG. 13A), increasing to minimal numbers of buckles at higher bending curvatures. However, cusps crosslinked with glutaraldehyde fixation produced numerous buckles (approximately 6-7) at low curvatures (FIG. 13B). EDC-crosslinked cusps had lower numbers of buckles than glutaraldehyde-crosslinked cusps at lower curvature (FIG. 13C). Neomycin trisulfate-bound leaflets experienced minimal to no buckling at low curvatures compared to other chemically crosslinked cuspal groups at similar bending curvatures (FIG. 13D). The number of buckles is only compared at low curvatures; as, at high curvatures, due to space limitations, the number of buckles is reduced and buckling depth becomes physiologically irrelevant.

FDA regulation for bioprosthetic heart valves suggests that the valves be fatigue cycled for 200 million fatigue cycles. BHVs have to pass this stern test in order to be used in valve replacement surgeries. In order to determine the durability of the valves to these fatigue cycles, the porcine aortic roots fixed in different fixatives were first prepped before cycling. The prepping involved careful trimming and suturing of the roots to flexible stents. These stented valves were mounted onto the M6 Dynatek Delta tester. 0.2% glutaraldehyde was used as the circulating medium in the tester.

The efficacy of neomycin trisulfate to resist tissue buckling by stabilizing valvular GAGs was evaluated following the in vitro cyclic fatigue. To determine the effect of cyclic fatigue on valvular tissue buckling behavior, glutaraldehyde crosslinked and neomycin-trisulfate-bound cusps were subjected to various radii of curvatures after undergoing 10 million accelerated fatigue cycles. Alternatively, another set glutaraldehyde-crosslinked and neomycin-trisulfate-bound valves were stored under static conditions to discern the change in tissue buckling pattern, if any, due to cyclical fatigue only.

Figure 14:
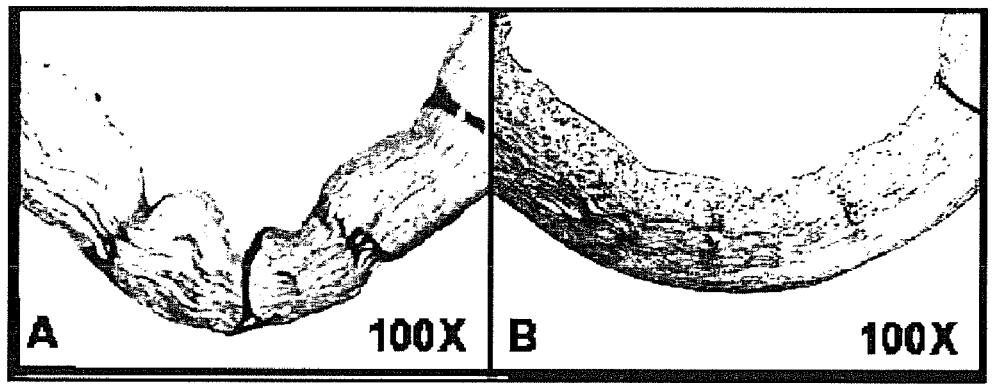
FIG. 14 provides histological evaluation of buckling behavior in glutaraldehyde crosslinked (FIG. 14A) and neomycin trisulfate bound (FIG. 14B) cusps bent to similar curvatures following 10 million fatigue cycles.

Upon histological observations, it was apparent that these cuspal tissues exhibited similar buckling patterns as seen previously (FIG. 14). Glutaraldehyde-crosslinked cusps, subjected to cyclic fatigue testing, buckled to a greater extent than those stored under static conditions when subjected to similar bending configurations (FIG. 14A). However, no substantial difference in buckling behavior was observed between neomycin-trisulfate-bound valvular tissues when subjected to fatigue cycling or when maintained in a static environment (FIG. 14B).

Figure 15A:
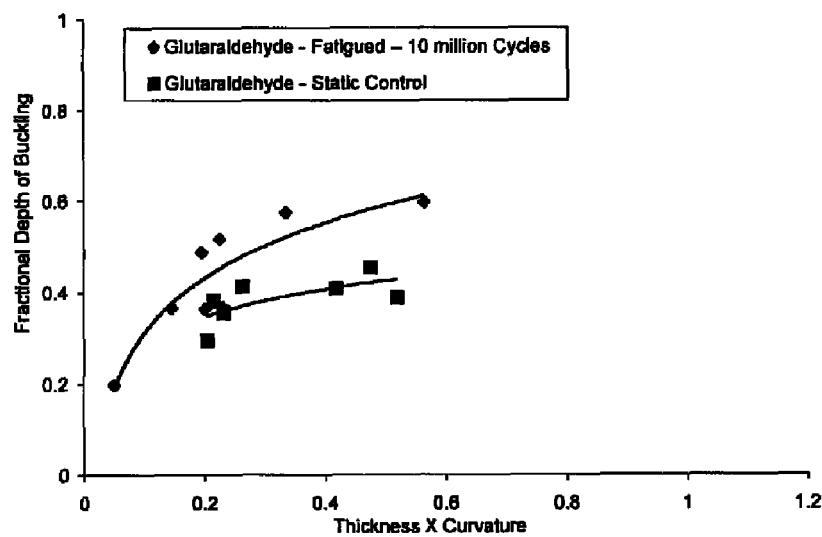
FIG. 15 provides graphical analyses of fractional depth of buckling for glutaraldehyde crosslinked (FIG. 15A) and neomycin trisulfate bound (FIG. 15B) cusps following subjection to increasing bending curvatures prior to (under static condition) and following 10 million fatigue cycles.
Figure 15B:
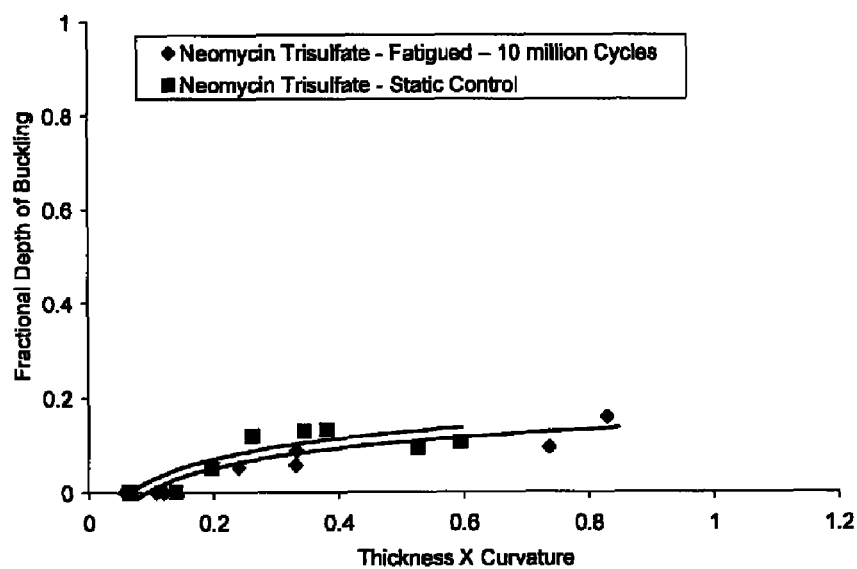

To quantitatively corroborate the abovementioned observations, graphical analyses of the cuspal groups was performed. In concurrence with the qualitative results, analogous tissue buckling behavior was obtained (FIGS. 15A and 15B), whereby fatigued neomycin-trisulfate-bound cusps experienced significantly lower fractional buckling depths than glutaraldehyde-crosslinked cusps with or without cyclical fatigue ($p<0.05$). Also, cusps with bound neomycin trisulfate exhibited no change in buckling behavior between statically stored and cyclically fatigued valves ($p>0.05$).

Figure 16A:
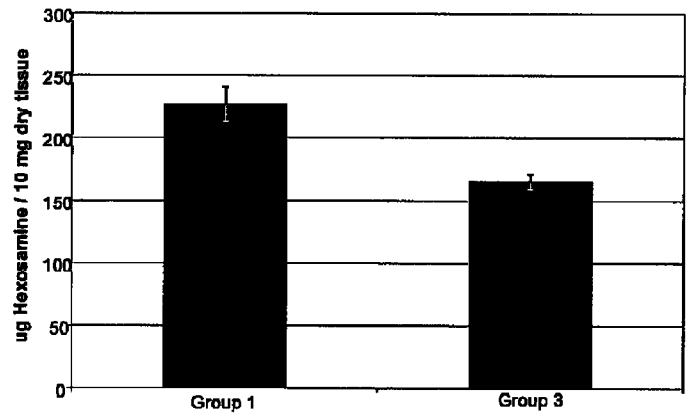
FIG. 16 illustrates the results following fatigue testing including hexosamine assay results following 10 million fatigue cycles (FIG. 16A), hexosamine assay results after different storage periods (FIG. 16B), and hexosamine assay results following 50 million fatigue cycles (FIG. 16C), for tissues treated as described herein.
Figure 16B:
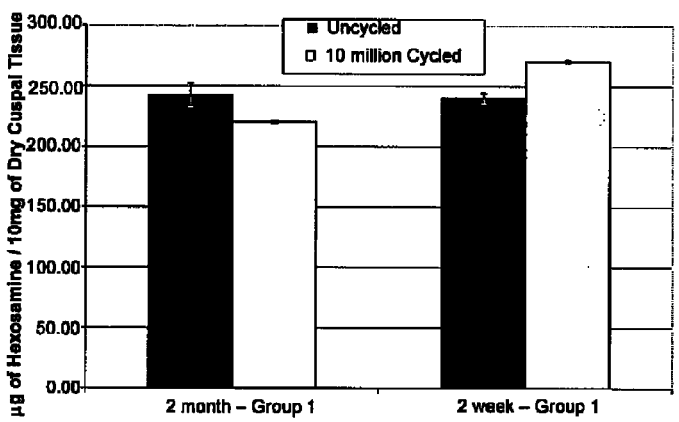
Figure 16C:
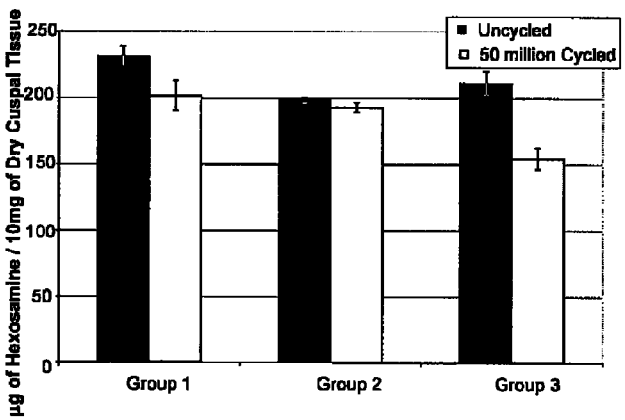

FIG. 16 shows the results of the fatigue testing (16A-16C). Hexosamine data on Group 1 (NEO) and Group 3 (GLUT) fixed valves after 10 million fatigue cycles suggests that GLUT loses more GAGs (FIG. 16A). In order to determine if storage had any effects during fatigue, Group 1 (NEO) fixed valves were stored for 2 weeks and 2 months (FIG. 16B) before fatigue cycling. 10 million fatigue cycles on those valves suggest that storage did not affect the NEO valves even after fatigue. FIG. 16C shows the valves cycled for 50 million fatigue cycles suggesting that Group 1 retained the most GAGs and Group 3 lost more GAGs. Comparing 16A and 16C, it can be seen that Group 3 lost more GAGs from 10 million to 50 million fatigue cycles.

Example 4

Disclosed treatment methods were coupled with an ethanol anti-calcification treatment. Porcine aortic heart valves were harvested as described above and three treatment protocols were carried out as follows:

GLUT-control group; 0.6% glutaraldehyde in HEPES buffer, pH 7.4 crosslinked for 24 h as previously described followed by 0.2% glut crosslinking for 6 additional days NEO-ethanol group; Neomycin-EDC/NHS treatment followed by GLUT, as described above in Example 1, followed by further treatment with 80% ethanol in HEPES buffer (pH 7.4) for 24 hours at room temperature.

GLUT-ethanol group; GLUT-treated tissues as previously described, followed by further treatment with 80% ethanol in HEPES buffer (pH 7.4) for 24 hours at room temperature.

Figure 17:
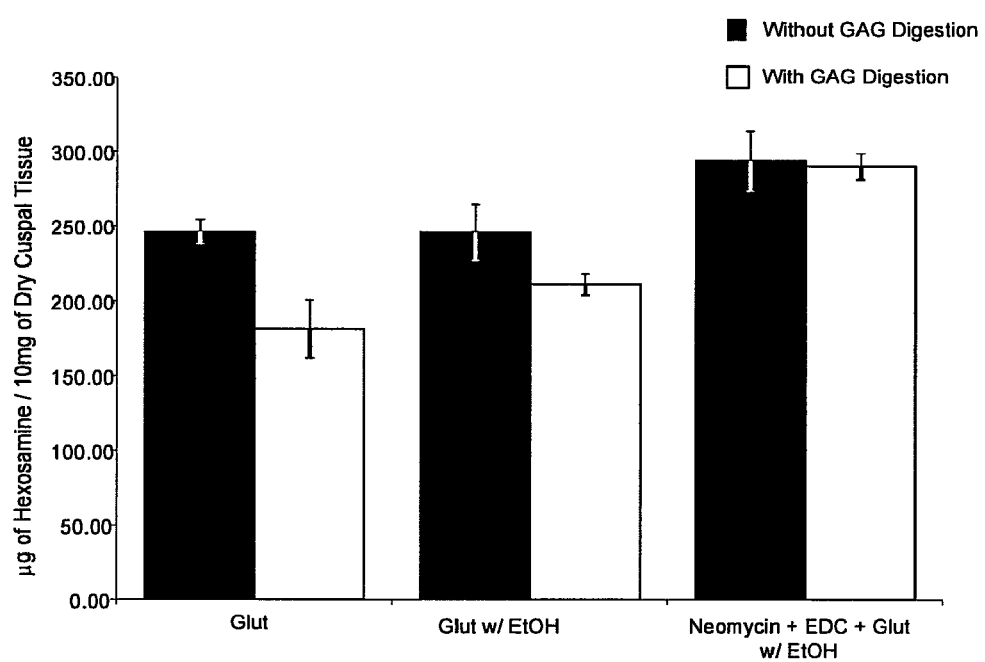
FIG. 17 illustrates the results of a hexosamine assay on materials treated as described herein and including an ethanol pre-treatment following fixation in glutaraldehyde and neomycin.

Pretreated cusps were incubated with 10 U/ml of hyaluronidase and 0.2 U/ml chondroitinase for 24 hours and hexosamine assay was then performed on the cusps. FIG. 17 shows the results of the hexosamine assay. As can be seen, the glutaraldehyde control and glutaraldehyde treated with ethanol cusps lost GAGs after enzyme digestion whereas the neomycin treated cusps including ethanol treatment still preserved and stabilized GAGs. This suggests that ethanol pretreatment did not cause loss of the GAG-degrading enzyme inhibition properties gained by the disclosed treatment methods and the properties of the tissue were not drastically changed.

Figure 18A:
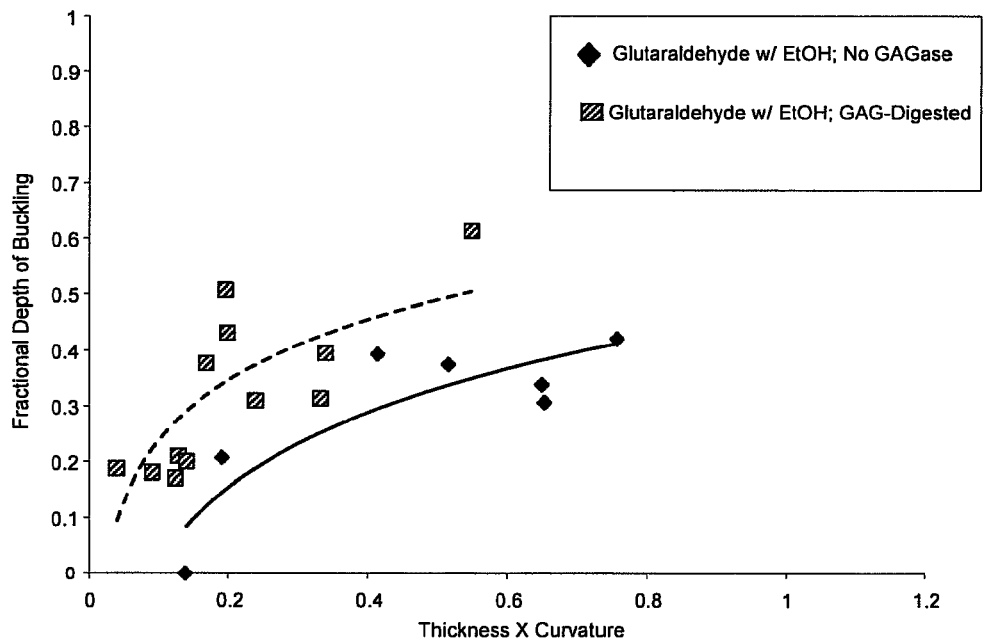
FIG. 18 illustrates the buckling data (FIGS. 18A and 18B) and the weight loss upon incubation with collagenase (FIG. 18C) and elastase (FIG. 18D) for materials treated as described herein including an ethanol pre-treatment.
Figure 18B:
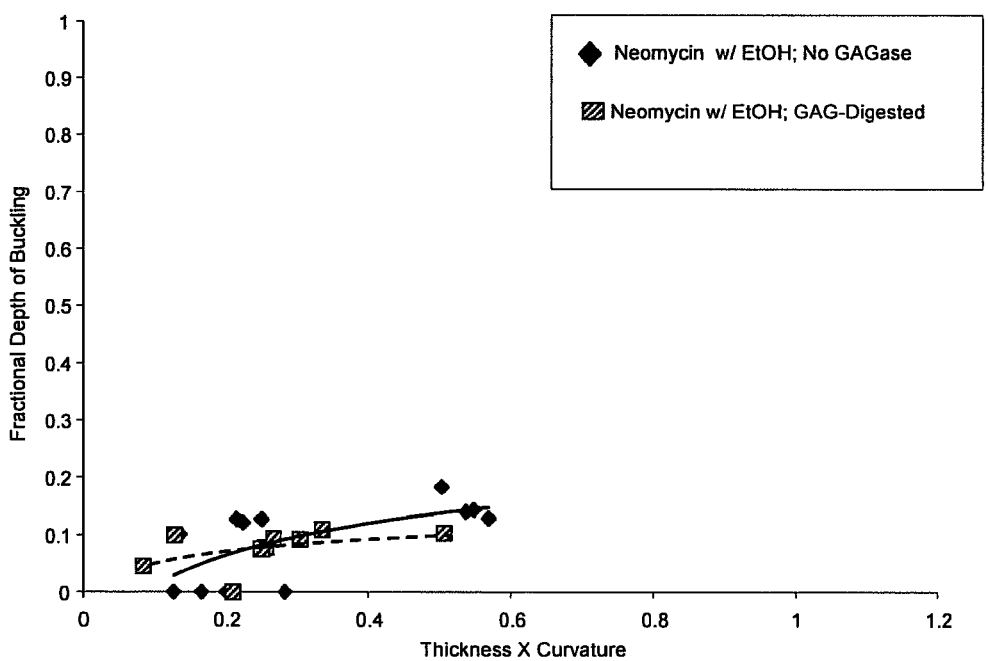

The treated cusps were subjected to reverse bending and various bending curvatures as described above in Example 3. FIGS. 18A and 18B show the fractional depth of buckling data after ethanol treatment for the ethanol and glutaraldehyde treated cusps (FIG. 18A) and the ethanol and neomycin+EDC+glutaraldehyde treated cusps (FIG. 18B). As can be seen, the glutaraldehyde treated cusps had greater depth of buckling than did the neomycin+EDC+glutaraldehyde treated cusps. The neomycin treated cusps did not experience any change in depth of buckling after GAG-degrading enzyme treatment whereas this increased significantly in the glutaraldehyde-only treated group.

Figure 18C:
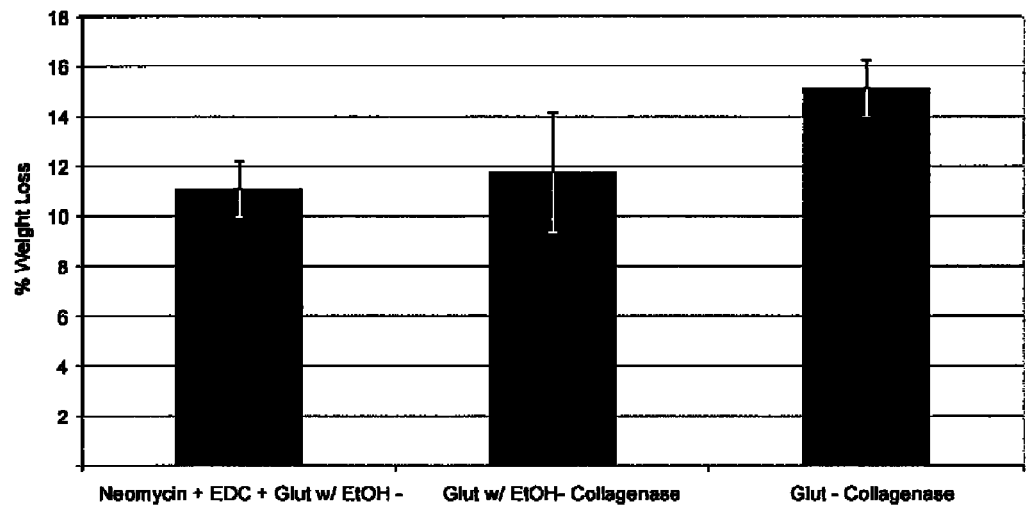
Figure 18D:
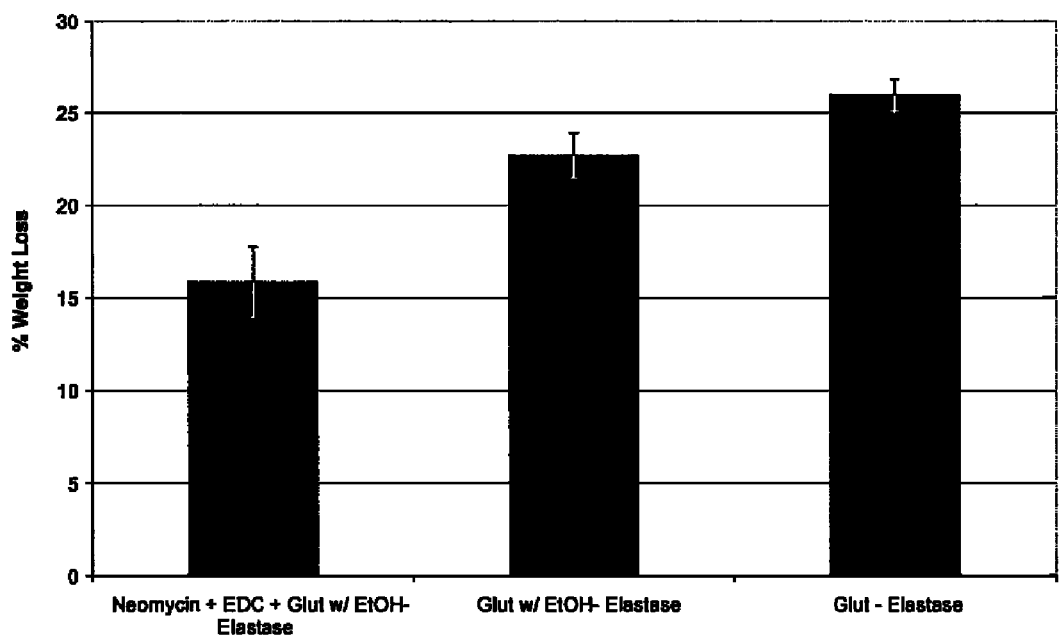

FIGS. 18C and 18D illustrate the amount of mass lost by the variously treated cusps following incubation with collagenase (FIG. 18C) and elastase (FIG. 18D) as described above in Example 3. As can be seen, the neomycin treated cusps that were also treated with ethanol lost the least mass as compared to other groups.

Example 5

Figure 19:
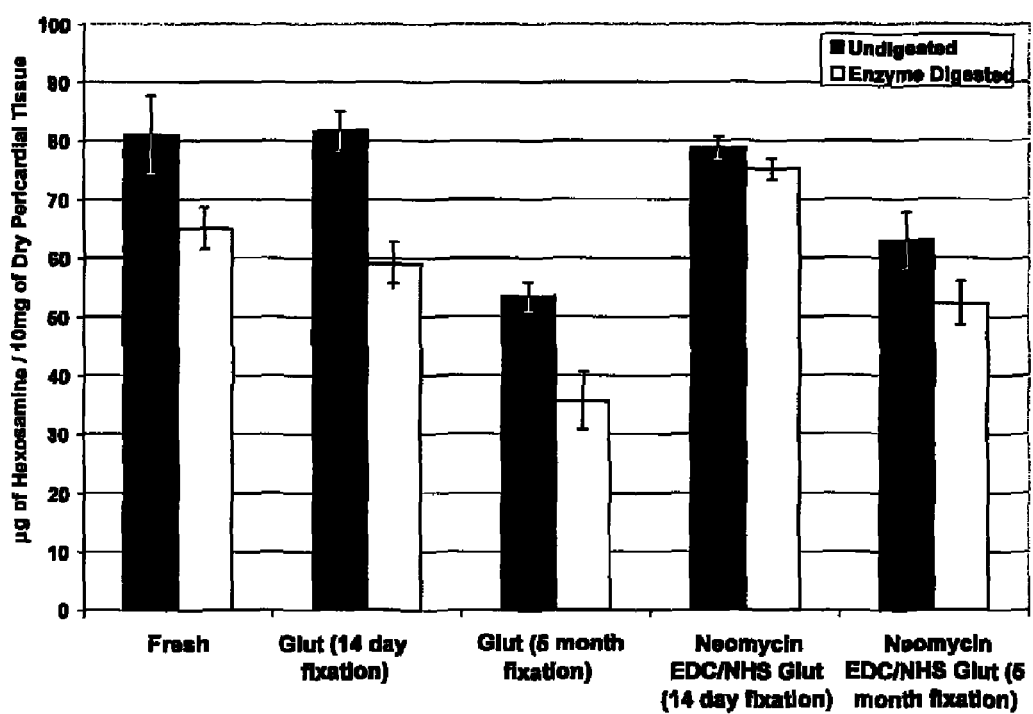
FIG. 19 is a graph setting forth the effect of enzyme digestion on pericardial tissue treated as described herein.

Pericardial tissue was treated with neomycin+EDC+glutaraldehyde as described above in Example 1 or with glutaraldehyde in order to examine treatment methods for effectiveness for GAG stabilization in this tissue type. Treated tissue was incubated in a solution containing 10 U/ml of hyaluronidase and 0.2 U/ml chondroitinase for 24 hours and hexosamine assay was then performed on the tissue. Results are shown in FIG. 19. Results suggest that fresh pericardial tissue is susceptible to GAG-degrading enzyme. Also, it can be seen that glutaraldehyde treated tissue progressively lost more GAGs during storage, suggesting that glutaraldehyde treatment alone did not stabilize GAGs in pericardial tissue. Neomycin treated tissue, however, effectively stabilized the GAGs against degrading enzymes and preserved the most GAGs even after 5 months of storage.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged, both in whole and in part. Therefore, the spirit and scope of the appended claims should not be limited to the description of the preferred versions contained therein.

What is claimed is:

1. An implantable tissue comprising a non-endogenous sulfated oligosaccharide enzyme inhibitor covalently bonded to the tissue, the enzyme inhibitor sterically or chemically preventing an enzyme from degrading a component of the tissue, wherein the component is a glycosaminoglycan and the enzyme inhibitor is bound to the component.

2. The implantable tissue of claim 1, wherein the enzyme inhibitor is a salt of neomycin.

3. The implantable tissue of claim 1, wherein the glycosaminoglycan is covalently bound in the tissue.

4. The implantable tissue of claim 1, the tissue further comprising crosslinked proteins.

5. The implantable tissue of claim 1, wherein the tissue is derived from xenograft, allograft, or autologous tissue.

6. The implantable tissue of claim 1, wherein the implantable tissue is a cardiovascular implant.

7. The implantable tissue of claim 1, wherein the implantable tissue is pericardial tissue or blood vessel tissue.

8. The implantable tissue of claim 7, wherein the implantable tissue is aortic tissue.

9. An implantable bioprosthetic comprising:
    an implantable tissue comprising a non-endogenous sulfated oligosaccharide enzyme inhibitor covalently bonded to the tissue, the enzyme inhibitor sterically or chemically preventing an enzyme from degrading a component of the tissue, wherein the component is a glycosaminoglycan and the enzyme inhibitor is bound to the component; and
    a support structure attached to the implantable tissue.

10. The implantable bioprosthetic of claim 9, wherein the enzyme inhibitor is a salt of neomycin.

11. The implantable bioprosthetic of claim 9, wherein the glycosaminoglycan is covalently bound in the tissue.

12. The implantable bioprosthetic of claim 9, the tissue further comprising crosslinked proteins.

13. The implantable bioprosthetic of claim 9, wherein the bioprosthetic is a bioprosthetic heart valve.

14. The implantable bioprosthetic of claim 9, wherein the tissue is derived from xenograft, allograft, or autologous tissue.

15. An implantable tissue comprising a sulfate salt of neomycin covalently bonded to the tissue, the tissue comprising glycosaminoglycan, the sulfate salt of neomycin sterically or chemically preventing an enzyme from degrading the glycosaminoglycan of the tissue, wherein the neomycin or a salt of neomycin is bound to the glycosaminoglycan.

16. The implantable tissue of claim 15, the tissue further comprising crosslinked proteins.

* * * * *

UNITED STATES PATENT AND TRADEMARK OFFICE
CERTIFICATE OF CORRECTION

PATENT NO. : 8,142,805 B1  
APPLICATION NO. : 11/934844  
DATED : March 27, 2012  
INVENTOR(S) : Narendra R. Vyavahare and Devanathan Raghavan Page 1 of 1

It is certified that error appears in the above-identified patent and that said Letters Patent is hereby corrected as shown below:

Column 1, lines 17 - 19 states,

"The United Stated Government may have rights in this invention pursuant to Contract No. HL 070969 between Clemson University and the National Institutes of Health."

Correct this paragraph to read as follows:

-- The United States Government has rights in this invention pursuant to Grant No. NIH HL070969 and Grant No. NIH HL108330 between Clemson University and the National Institutes of Health. --

Signed and Sealed this  
Twelfth Day of January, 2016

Michelle K. Lee  
*Director of the United States Patent and Trademark Office*

UNITED STATES PATENT AND TRADEMARK OFFICE
CERTIFICATE OF CORRECTION

PATENT NO. : 8,142,805 B1
APPLICATION NO. : 11/934844
DATED : March 27, 2012
INVENTOR(S) : Narendra R. Vyavahare and Devanathan Raghavan Page 1 of 1

It is certified that error appears in the above-identified patent and that said Letters Patent is hereby corrected as shown below:

In the Specification

Column 1, lines 17 - 19 states,

"The United States Government may have rights in this invention pursuant to Contract No. HL 070969 between Clemson University and the National Institutes of Health."

Please correct this paragraph to read as follows:

-- This invention was made with government support under grant #HL070969 and grant #HL108330 awarded by The National Institutes of Health. The government has certain rights in the invention. --

Signed and Sealed this
Twelfth Day of July, 2016

Michelle K. Lee
*Director of the United States Patent and Trademark Office*